United States Patent [19]
Goffe

[11] Patent Number: 5,622,857
[45] Date of Patent: Apr. 22, 1997

[54] HIGH PERFORMANCE CELL CULTURE BIOREACTOR AND METHOD

[75] Inventor: Randal A. Goffe, Arlington, Wash.

[73] Assignee: Genespan Corporation, Redmond, Wash.

[21] Appl. No.: 512,546

[22] Filed: Aug. 8, 1995

Related U.S. Application Data

[63] Continuation-in-part of PCT/US94/02140 Feb. 9, 1994.

[51] Int. Cl.⁶ .............................. C12N 5/00; C12M 3/06
[52] U.S. Cl. ................. 435/378; 435/297.4; 435/299.1; 435/380; 435/398; 435/400; 435/402; 210/321.8
[58] Field of Search .............................. 435/289.1, 297.4, 435/299.1, 240.242, 240.241, 240.23; 422/48; 210/321.8, 321.89

[56] References Cited

U.S. PATENT DOCUMENTS

| | | | |
|---|---|---|---|
| 3,536,611 | 10/1970 | de Filippi et al. ........................ | 210/22 |
| 3,821,087 | 6/1974 | Knazek et al. ........................... | 195/127 |
| 3,883,393 | 5/1975 | Knazek et al. ........................... | 195/1.8 |
| 4,061,736 | 12/1977 | Morris et al. ............................ | 424/177 |
| 4,184,922 | 1/1980 | Knazek et al. ........................... | 435/284 |
| 4,220,725 | 9/1980 | Knazek et al. ........................... | 435/285 |
| 4,329,431 | 5/1982 | Youssef .................................. | 435/253 |
| 4,537,860 | 8/1985 | Tolbert et al. .......................... | 435/240 |
| 4,720,462 | 1/1988 | Rosenson ................................ | 435/289 |
| 5,278,063 | 1/1994 | Hubbell et al. .................. | 435/240.243 |
| 5,290,700 | 3/1994 | Binot et al. ............................. | 435/284 |
| 5,459,058 | 10/1995 | Leder et al. .......................... | 435/240.2 |

FOREIGN PATENT DOCUMENTS

| | | | |
|---|---|---|---|
| 0419234A2 | 3/1991 | European Pat. Off. . | |
| 63-59879 | 3/1988 | Japan ..................................... | 435/284 |
| 63-240774 | 10/1988 | Japan ..................................... | 435/284 |
| 1-222768 | 9/1989 | Japan ..................................... | 435/284 |
| 63-317075 | 12/1989 | Japan ..................................... | 435/284 |
| 2-245176 | 9/1990 | Japan ..................................... | 435/284 |
| WO86/06094 | 10/1986 | WIPO .................................... | 435/284 |
| WO90/13639 | 11/1990 | WIPO .................................... | 435/284 |
| WO92/11355 | 7/1992 | WIPO .................................... | 435/285 |
| WO95/21911 | 8/1995 | WIPO . | |

OTHER PUBLICATIONS

Custer, L.M., Ph.D. Chem. Engr. Dissertation: Physiological studies of hybridoma cultivation in hollow fiber bioreactors, UCB, 1988 pp. 15, 49, 69, 83, 103, 106–108, 115, 181–182, 193–197, 201, and 221–223.

Oudshoorn, A., Presentation Multiple Fiber Bioreactor on distributor training, Dec. 10, 1991.

Oh, D.J., et al., High density culture of hybridoma cells in a dual hollow fiber bioreactor, *Biotechnology Techniques*, 6(1):77–82, 1992.

Fresenias, A.G., et al., Autoklavierbares Hollow Fiber Bioreaktormodul mit integrierter Basgasung, Biotech GmbH & Co., 1993.

Hohlfaser–Reaktor für Humanzellen, *B–L Journal*, 4:3, Jul. 1993.

Cousins, R.B., et al., A dual fibre membrane reactor for the cultivation of mammalian cells.

*Primary Examiner*—William H. Beisner
*Attorney, Agent, or Firm*—Christensen O'Connor Johnson & Kindness PLLC

[57] ABSTRACT

A high performance hollow fiber bioreactor having concentric hollow fiber bundles: a central hollow fiber bundle supplies media, and an outer array supplies oxygen needed for cell culture. Useful to expand therapeutic cells such as stem cells ex vivo, and as an extracorporeal device such as an artificial liver.

46 Claims, 18 Drawing Sheets

HIGH PERFORMANCE CELL CULTURE BIOREACTOR AND METHOD

STATEMENT OF RELATED APLICATIONS

This applicstion is a continuation-in-part of international appliation Ser. No. PCT/US94/02140, filed Feb. 9, 1994.

FIELD OF THE INVENTION

This invention relates to hollow fiber bioreactors. More particularly, this invention relates to a novel high performance bioreactor and to a method for its utilization in the fields of production of biopharmaceuticals, expansion of cells, and genetic transformation and harvesting of target cells.

BACKGROUND OF THE INVENTION

Prior art bioreactors conventionally perfuse nutrient media through a single type of hollow fiber. The various disadvantages of such bioreactors include heterogeneous cell mass, difficult procurement of representative cell growth samples, and poor performance due to inefficient oxygenation and an inability to control oxygen levels. Moreover, microenvironmental factors such as pH cannot be effectively controlled. Mixed culture or co-culture of cells is not possible.

DEFINITIONS

In the specification and claims, the following terms have the meaning set forth below.

HPBr—High Performance Bioreactor.

Extracapillary Space (ECS)—The space within the bioreactor cartridge which is not occupied by the hollow fibers.

Intracapillary Space (ICS)—The totality of the space defined by the lumens of the hollow fibers in a bioreactor.

OXY-1—A hollow fiber oxygenator available from Uni-Syn Technologies, Inc., 14272 Franklin Avenue, Suite 106, Tustin, Calif. 92680. The OXY-1 oxygenator is provided with 0.2 μm pore size polyethylene hollow fibers woven to form a mat. The active surface area for gas exchange is 1 ft².

BR110—A small hollow fiber bioreactor commercially available from UniSyn Technologies, Inc. The BR110 hollow fibers are cellulosic, with 10 kD molecular weight cutoff (MWc). The active surface area for cell growth is 1.5 ft².

Micro Mouse BR110—A sterile disposable bioreactor device equipped with a BR110 bioreactor with a length of silicone tubing in the ICS loop for gas exchange; available from UniSyn Technologies, Inc.

Cell-Pharm 1000—A hollow fiber bioreactor instrument commercially available from UniSyn Technologies, Inc. The Cell-Pharm 1000 system includes a controller, pH sensor, gas mixture control capability, media reservoir, heater and peristaltic pump and pinch valves.

MAb—Monoclonal antibody.

Mitsubishi Oxygenator Fibers—0.2 μm pore size polypropylene single strands of hollow fibers from Mitsubishi, Japan.

Microgon fibers—0.2 μm pore size mixed cellulose ester hollow fiber from Microgon, Inc., Laguna Hills, Calif.

Graphite/Ceramic tube—0.14 μm pore size Carbosep™ tubular membrane from Rhône-Poulenc, Inc., Cranbury, N.J.

Glucose Utilization Rate (CUR)—The rate at which glucose is consumed from the nutrient media in a batch feed system (in units of mass per unit time, e.g., gm/day) on the day prior to the current sample. This is derived as follows:

$GUR = F(G_f - G) + V(G_1 - G)$, $G = (G_1 + G_2)/2$ where $G_f$ is the glucose concentration in ICS media feeding (i.e., 4.1 g/L); $G_1$, the glucose concentration (g/L) in ICS recirculating media on the day prior to the current sample; $G_2$, the glucose concentration (g/L) in ICS recirculating media in the current sample; F, the ICS media feeding rate (L/day); and V, the volume of ICS media in reservoir (L).

Lactate Production Rate (LPR)—The rate at which lactate (or lactic acid) is produced anaerobically while glucose is consumed. Therefore, one molecule of glucose produces two molecules of lactic acid without oxygen involved in the reaction. Lactate production rate (LPR), g/day, is defined as:

$LPR = [F(L - L_f) + V(L - L_1)] \times 0.09$, $L = (L_1 + L_2)/2$ where $L_f$ is the lactate concentration in intracapillary (ICS) media (i.e., 0.1 mM); $L_1$, the lactate concentration (mM) in ICS recirculating media on the date prior to the current sample; $L_2$, the lactate concentration (mM) in ICS recirculating media.

SUMMARY OF THE INVENTION

It has been discovered that inefficient oxygenation is a focal constraint upon the efficiency of hollow fiber cell culture devices. The invention provides a novel bioreactor and extracorporeal device which achieves greatly enhanced nutrient media oxygenation as compared with prior art devices. Further, the invention provides a nutrient media containing a relatively high concentration of a free radical scavenger (i.e., up to 0.05 M), which enhances metabolic efficiency, productivity and cell mass expansion. Physiological processes, such as glycosylation, that are dependent upon oxygenation level are enhanced and facilitated.

The subject bioreactor has a housing with an inner wall defining a substantially tubular cell culture chamber. First and second ends of the housing define a longitudinal axis through the chamber. At least one port provides access to the chamber. Pursuant to the invention, a central bundle of porous hollow fibers is disposed around the longitudinal axis within the chamber, and an annular bundle of gas permeable hollow fibers is disposed concentric to and surrounding the central bundle. Means are disposed at the first and second ends for passing nutrient media through the porous hollow fibers, and for passing an oxygen containing gas through the gas permeable hollow fibers. An annular space is typically provided between the inner wall and the annular bundle of oxygenator fibers. An annular space may alternatively or also be provided between the annular bundle and the central bundle of nutrient media fibers. Microcarriers for culture of anchorage dependent cells may be disposed within the annular space(s).

Three categories of bioreactors are provided for different purposes. In bioreactors of category I, the ratio of the surface area of the gas permeable hollow fibers to the surface area of the porous hollow fibers is from about 0.5 to about 3.1, and the gas permeable hollow fibers and the porous hollow fibers collectively occupy from about 10 to about 40 percent by volume of the cell culture chamber. Such bioreactors are optimal for cell expansion and harvesting, particularly for culturing anchorage dependent cells on microcarriers. Category I can in turn be subdivided. In bioreactors of category Ia, the hollow fiber surface area ratio is from about 0.5 to about 1.5, and the hollow fibers collectively occupy from about 10 to about 25 percent by volume of the cell culture chamber. Such category Ia bioreactors are particularly suitable for slow growing cells that have relatively low oxygen requirements and/or cells that are particularly sensitive to oxygen free radicals. In bioreactors of category Ib, the surface area ratio is from about 1.5 to about 3.1, and the fibers collectively occupy from about 25 to about 40 percent by volume of the chamber. Such category Ib bioreactors are particularly suitable for cells with average or particularly high oxygen requirements.

In bioreactors of category II, the ratio of the surface area of the gas permeable hollow fibers to the surface area of the porous hollow fibers is from about 3.1 to about 4, and the gas permeable hollow fibers and said porous hollow fibers collectively occupy from about 40 to about 50 percent by volume of the cell culture chamber. Bioreactors of category II provide for highly efficient metabolite production and are particularly useful as extracorporeal devices.

In bioreactors of category III, the ratio of the surface area of the gas permeable hollow fibers to the surface area of the porous hollow fibers is from about 4 to about 5.8, and the gas permeable hollow fibers and the porous hollow fibers collectively occupy from about 50 to about 70 percent by volume of the cell culture chamber. Bioreactors of category III are characterized by relatively low efficiency metabolite production, but may be used for production of biomolecules such as monoclonal antibodies or TPA.

The invention also provides cell culture kits which include a bioreactor and a plurality of microcarriers, which may be coated with an extracellular matrix molecule.

The invention also provides an improved method of cell culture: Cells are introduced into the cell culture chamber of the subject bioreactor; and the cells are incubated within the chamber while passing an oxygen containing gas through the gas permeable hollow fibers and while passing nutrient media through the porous hollow fibers. Thereafter the cells and/or their products are harvested from the chamber. In operation, the passage of oxygen containing gas through the gas permeable hollow fibers is preferably counter current to the passage of nutrient media through the porous hollow fibers; and the bioreactor is periodically rotated to-and-fro by about 120 degrees around its longitudinal axis. The nutrient media preferably contains a free radical scavenger, such as sodium benzoate or benzoic acid. The free radical scavenger is typically provided in the nutrient media at a concentration of from about 0.001 to about 0.1 M, and the nutrient media is buffered to maintain pH at about 7.1. The oxygen containing gas is passed through the gas permeable hollow fibers at a pressure low enough, typically from about 0.5 to about 1.5 psi, to avoid formation of gas bubbles within the cell culture chamber.

Where the bioreactor has an outer annular space between the inner wall and the annular bundle, the cells (and, permissibly, microcarriers) are simply introduced through the port into the annular space. Such introduction or inoculation is typically effected using a syringe and hypodermic needle. A similar inoculation procedure is used where the bioreactor has an inner annular space, between the annular bundle and the central bundle. For convenient harvesting of cells, the bioreactor may be provided with a first port adjacent the first end and a second port adjacent the second end, in which case harvesting is by introducing a gas through the first port into the chamber and thereby displacing medium containing cells (and microcarriers) from the chamber through the second port. For efficient harvesting of anchorage dependent cells, a cell detachment (i.e., proteolytic) enzyme, such as trypsin or collagenase may first be introduced into the chamber.

The subject high performance bioreactors are particularly suited for the cultivation of oxygen intensive cells, such as hepatocytes, as well as insect cells for production of biomolecules for commercial purposes. Production of viral vectors and the process of gene transfection are likewise enhanced and facilitated using the subject bioreactors.

DETAILED DESCRIPTION OF THE PREFERRED EMBODIMENT

Pursuant to the invention, nutrient media is supplied through an inner passage concentric to and hence surrounded by an outer bundle of oxygenator hollow fibers. The inner media passage is provided by a single media-porous tube or by an inner bundle of media supply hollow fibers. The exterior surface of the outer or oxygenator fiber bundle is preferably spaced from the inner wall of the bioreactor housing to facilitate the mixing of cellular material and the sampling or harvesting of product cells.

CONSTRUCTION OF THE HIGH PERFORMANCE BOREACTOR

This portion of this specification describes, by reference to the FIGURES, the best mode presently known to the inventor for the construction of a bioreactor which embodies the invention.

Figure 1:
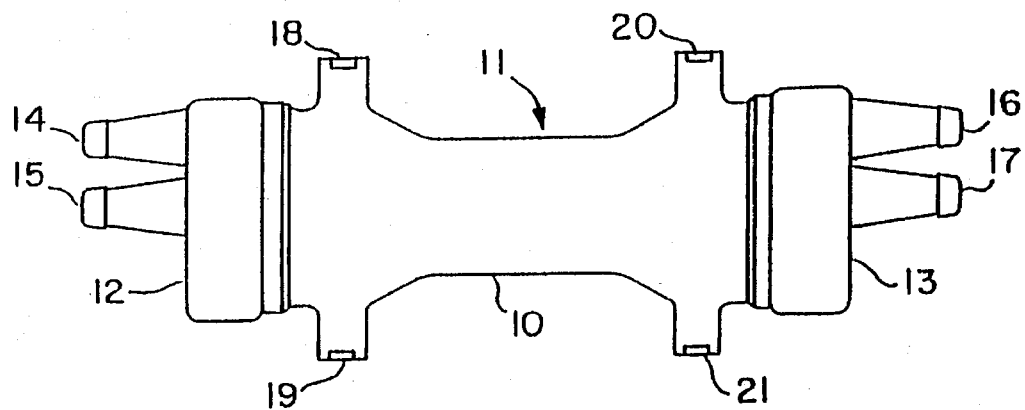
FIG. 1 is a schematic illustration of a bioreactor of the invention.

Referring to FIG. 1, the bioreactor 10 includes a housing 11 having substantially identical headers 12 and 13 at its input and output ends. Headers 12 and 13 have ports 14, 15, 16 and 17 for the introduction and withdrawal of oxygen containing gas and media.

Figure 2A:
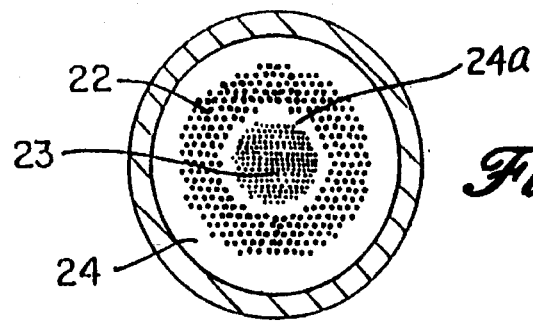
FIG. 2A is a cross-section of a center section of a bioreactor as shown by FIG. 1.
Figure 2:
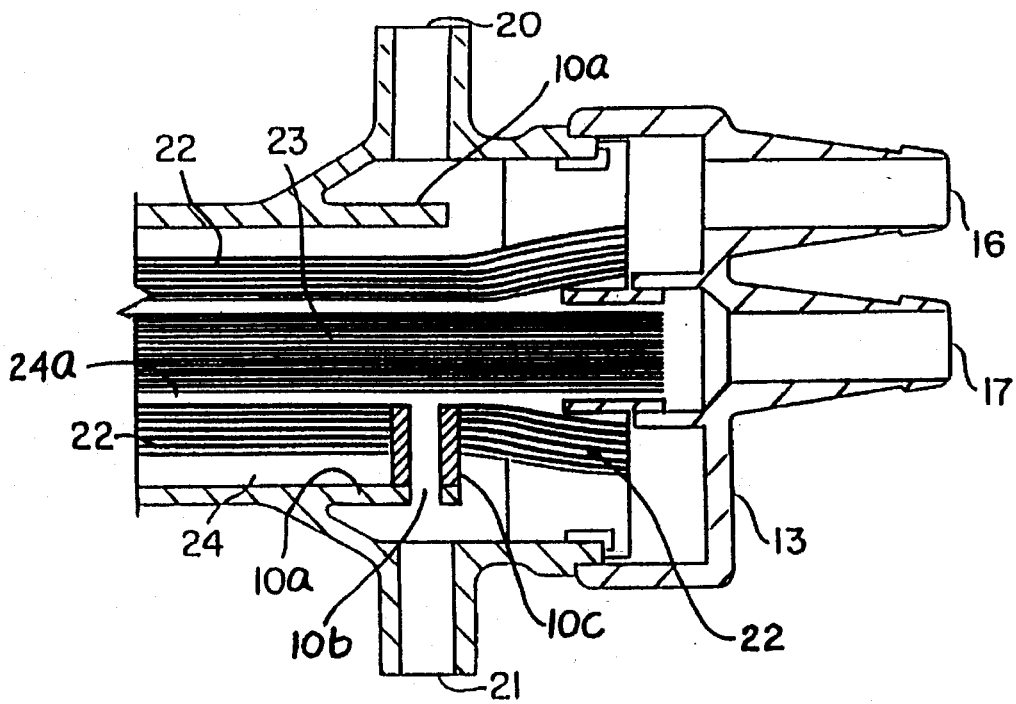
FIG. 2 is a cross-section of one of two substantially identical ends of a bioreactor as shown by FIG. 1.

FIGS. 2 and 2A illustrates an outer oxygenator fiber bundle 22 concentric with an inner media supply fiber bundle 23. The exterior periphery of the oxygenator bundle 22 is separated by an annular space 24 from the inner wall of the housing 11. tteader ports 14 and 16 accommodate the introduction of oxygen containing gas into and withdrawal of oxygen containing gas from the oxygenator fibers 22. Header ports 15 and 17 accommodate the passage of nutrient media into and the removal of nutrient media from the nutrient media supply fibers 23.

Product cells or proteins are typically sampled and harvested from space 24 through one of the ports, such as port 20 shown in FIG. 2. The housing 10 may be provided with a flow distributor plate 10a, positioned between the port 20 and the oxygenator fibers 22, which serves to distribute the flow of material introduced through the port and also protects the fibers 22 from damage when cells are introduced into the space, e.g., with a hypodermic needle. For certain applications the cells may be introduced into an inner annular space 24a, situated between the media supply fibers 23 and the oxygenator fibers 22. For this purpose, plate 10a may be provided with a port 10b to permit passage of a hypodermic needle through oxygenator fiber bundle 22 and into the inner annular space 24a. A tubular guide 10c may optionally be provided on the inner surface of plate 10a to protect the oxygenator fibers 22 from damage by the inoculating needle (not shown).

A preferred method of fabricating a bioreactor embodying the invention includes six major steps now described by reference to FIGS. 3 to 10.

1. Prepare 4¾ inch length fiber bundles from fiber tows with the requisite number of strands. Wrap the end of each bundle with tape so that fibers are held securely.

Optionally, the jacket is modified by drilling a hole through the flow distributor plate inside one or more of the ports. A cylinder shaped member is attached to the inner side of the flow distributor plate with polyurethane resin so that a hypodermic needle can pass freely through the port and the attached cylinder member.

Figure 3:
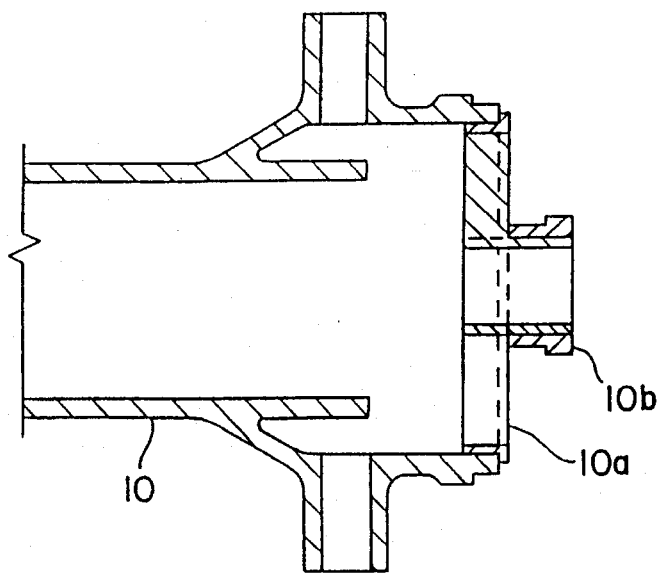
FIG. 3 depicts the hollow fiber housing and the critical components which enable efficient and scaleable fabrication of high performance bioreactor.

2. Assemble jacket (10) with the fiber guide (10d) and mask (10e) as shown in FIG. 3.

Figure 3A:
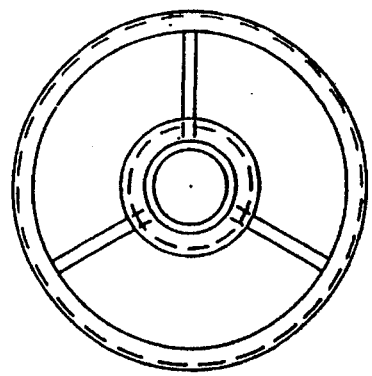
FIG. 3A is an end view of the hollow fiber housing of FIG. 3.

3. Preheat and prespin cellulose fiber bundles for 20 minutes at 1800 CPM and 52° C. to remove excess glycerine processing aid. Carefully insert cellulose fibers through the central hole in the fiber guides at each end of the jacket assembly shown in FIG. 3A. Similarly, put three bundles of oxygenator fibers through the three lateral holes in the fiber guide and ensure that they are loosely packed. Further drying of the bundles is done at 65° C. for 14–18 hours.

Figure 4:
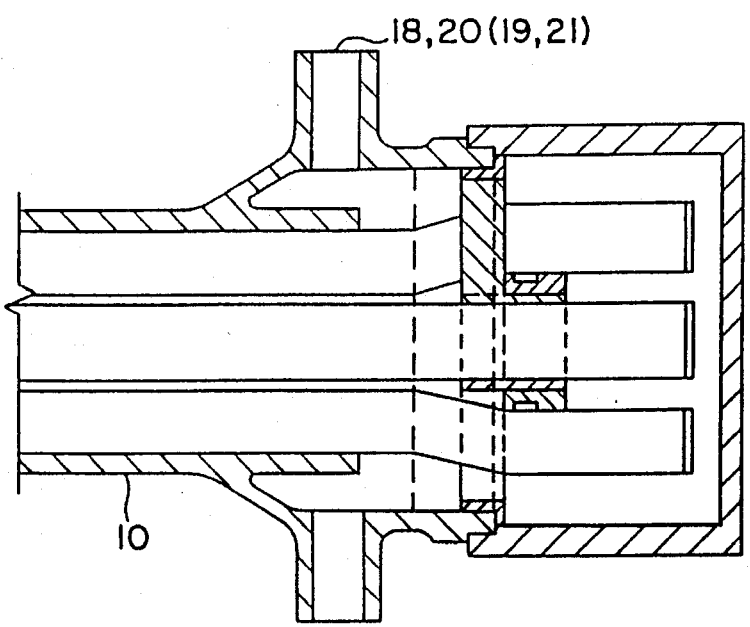
FIG. 4 shows the FIG. 3 assembly in the mold with potting compound.
Figure 5:
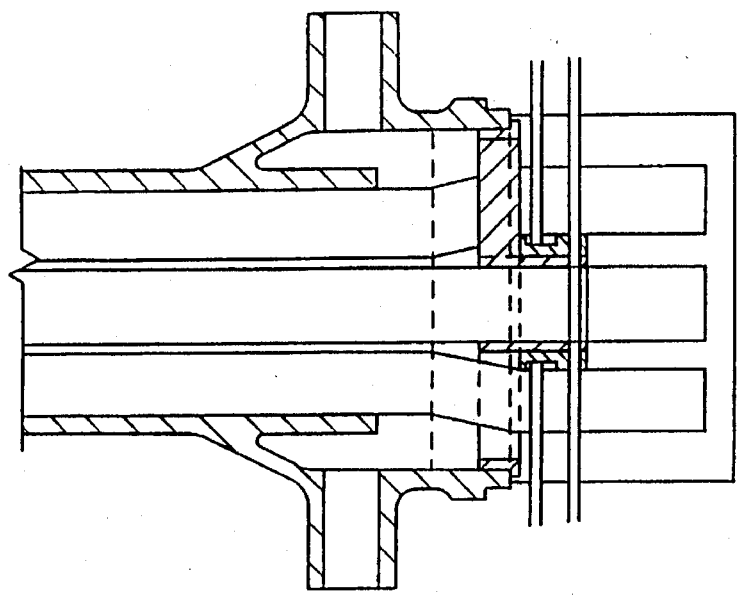
FIG. 5 illustrates the potted ends of the cartridge after removal from the mold, with the two cut marks for removal of excess adhesive and fiber indicated. Note that the mask component is sacrificial and is removed with excess adhesive. The hollow fiber guide remains imbedded in the adhesive as a permanent part of the end seal in the hollow fiber housing.
Figure 6:
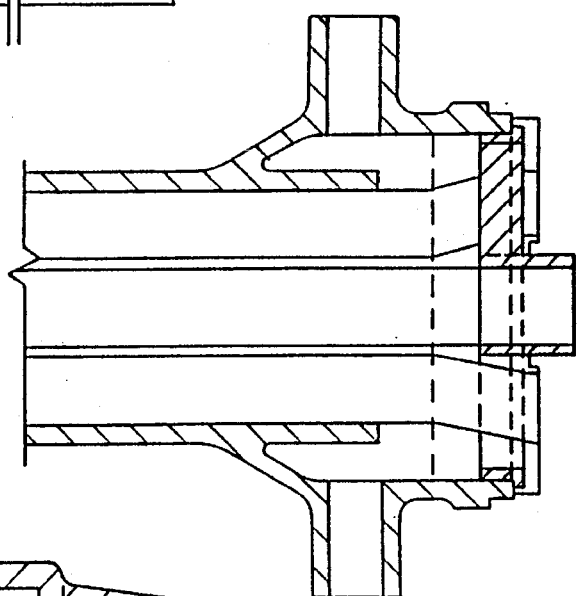
FIG. 6 depicts the cut end of the bioreactor cartridge.
Figure 7:
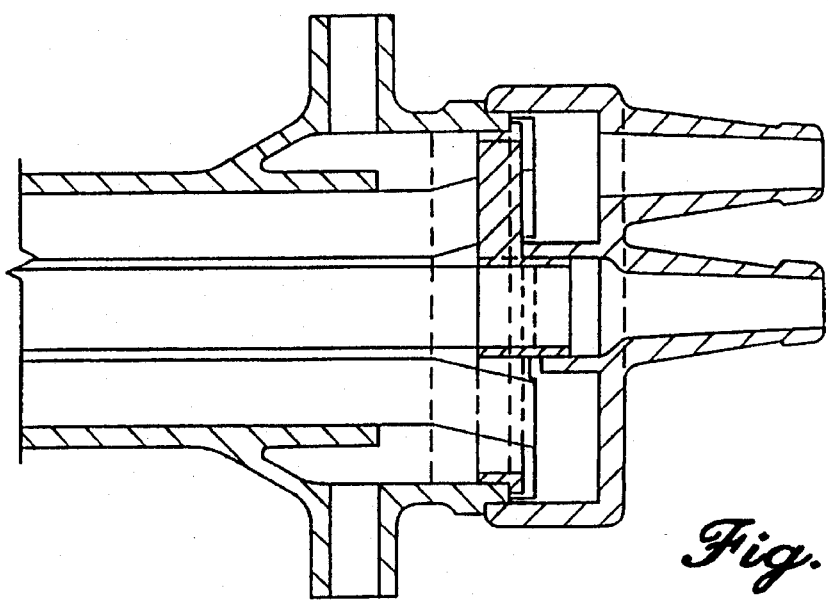
FIG. 7 shows the final assembly including the dual port header, which provides a means to supply media to the inner bundle of fibers and oxygen containing gas to the outer concentric ring of fibers.
Figure 8:
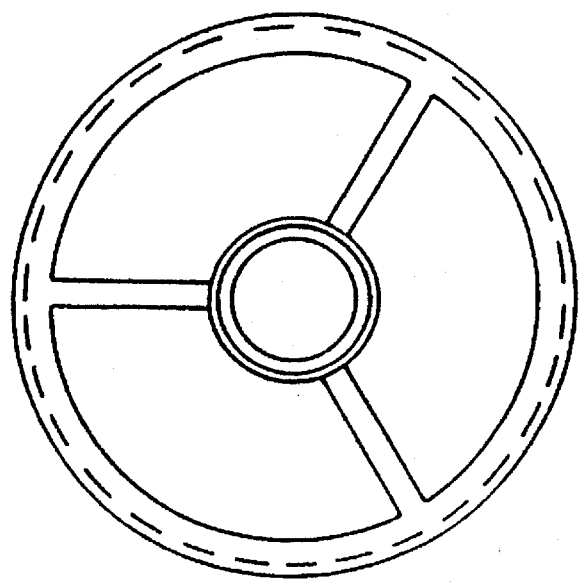
FIG. 8 is a detailed scale drawing of the fiber guide. This component provides the means for both organizing the two types of fibers, and enables sealing of the central fiber bundle to an independent port from that of the outer bundle of fibers.
Figure 8A:
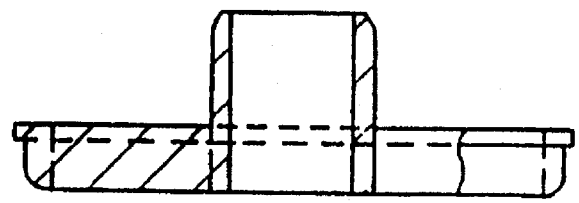
FIG. 8A is a side view of the fiber guide shown in FIG. 8.
Figure 9:
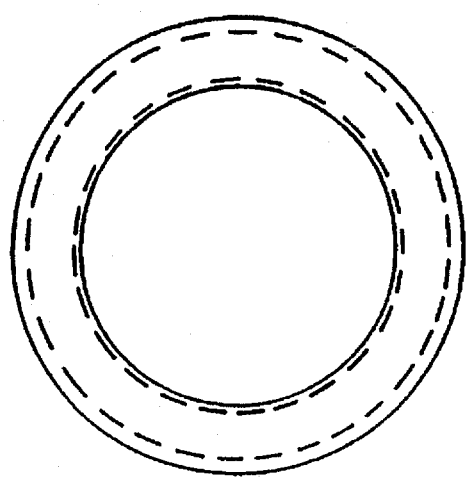
FIG. 9 is a detailed scale drawing of the sacrificial mask which fits over the portion of the fiber guide to provide a clean surface for sealing the central fiber bundle port.
Figure 9A:
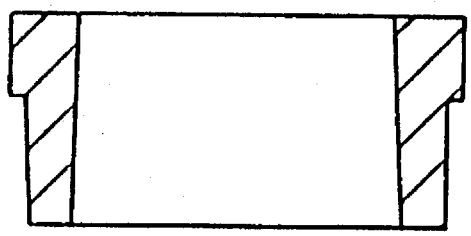
FIG. 9A is a side view of the mask shown in FIG. 9.
Figure 10:
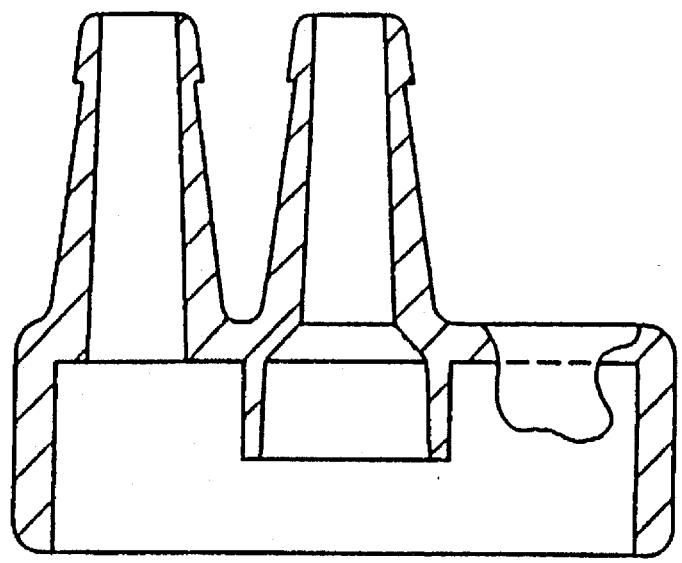
FIG. 10 is a detailed scale drawing of the dual port header for supplying media to the central bundle of fibers and oxygenated gas to the outer fibers independently.
Figure 10A:
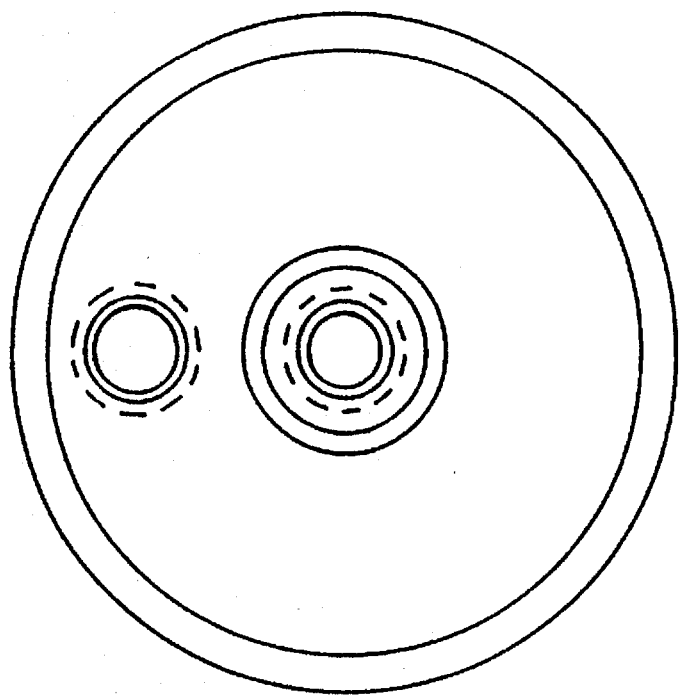
FIG. 10A is a top view of the header shown in FIG. 10.

4. Place the warm jacket/bundle assembly in a potting mold to encase the free ends of the bundles as shown in FIGURE 4. This assembly is placed in a centrifuge with premixed polyurethane resin in an applicator. Spin the entire assembly at 1500 CPM for 50–60 minutes at 38°–45° C.

The resin enters the jacket assembly (10) through either ports 18 and 20, or 19 and 21.

5. Cut the warm cured resin at the potted ends of the jacket/bundle assembly along the two "cut" lines shown in FIG. 5. Remove the cut pieces along with the mask (10e shown in FIG. 3), to expose the clean surface of the fiber guide (10d in FIG. 3). This surface participates in sealing the header.

6. The header is installed after applying polyurethane resin to the clean surface exposed by removing the mask, and to the outer rim of the jacket (10). Curing occurs at room temperature over a 24 hour period.

MEDIA SUPPLY FIBER TYPES

Hollow fibers represent a specific group of tubular articles that are within the scope of this invention. Therefore, any porous tube or fiber that is capable of being integrated into a recirculating (ICS) loop, while enabling perfusion of nutrient media to cells growing on the outside, is included in this invention. The following are examples of tubes or fibers preferred for use in this invention:

(i) Hollow fibers and tubes with dialysis, ultrafiltration and microfiltration properties, i.e., (a) molecular weight cutoff (MWc) ranging from 1 kD to 1,000 kD; and (b) pore size ranging from 0.01 μm to 5.0 μm. The most preferred range is from 10 kD MWc and about up to 1 μm pore size.

(ii) Materials of construction include polymers, graphite, ceramics (including porous glass fiber) and metals (e.g., stainless steel). Typically, polymers are required to have good physical properties (e.g., tensile strength, melt temperature and glass transition temperature). These include cellulose, polyethylene, polypropylene, polysulfone (and other engineering thermoplastics), polymethyl methacrylate, polyacrylonitrile, various polymer blends and the like. Specifically preferred media supply fibers are from cellulose polymers, have a MWc of 10–1,000 kD and a pore size of 0.01–1.0 μm.

OXYGENATOR FIBER TYPES

Hollow fibers are the only tubular configuration selected for oxygenation in this invention. These hollow fibers can be porous or non-porous. Porous hollow fibers for oxygenation are typically hydrophobic (like those made from polyethylene, polypropylene, polytetrafluoroethylene (Teflon™) and the like). Examples of non-porous hollow fibers include (but are not restricted to) silicone, and silicone copolymer capillary tubing. They typically have high gas permeability through the solid wall structure.

Porous hydrophobic hollow fibers are most effective for gas exchange when the pore size is in the range of 0.01 to 0.5 μm. Optimally, pore size should be in the range of 0.1 to 0.2 μm.

Specifically preferred oxygenator fibers are formed from polypropylene and a pore size of 0.15 μm.

DISCUSSION OF OPERATION

The HPBr is equipped with the means for recirculating nutrient media via the lumen (or ICS) of a hollow fiber bundle or other tubular structures centrally located in the bioreactor jacket. These hollow fibers or tubes are selected for their permeability properties, and in some instances for their surface properties (e.g., hydrophilicity or hydrophobicity). Media perfused through the porous wall of these structures bathe cells that have been inoculated in the ECS. When hydrophobic media fibers are used, relatively high transmembrane pressures are required to achieve equivalent perfusive flow of media into the ECS than with hydrophilic hollow fiber membranes.

$O_2/CO_2$ gas mixtures are supplied to the HPBr through the lumen tube or a bundle of hollow fibers that are situated concentric to the centrally placed hollow fibers or tubes. The gas mix preferably flows counter current to the flow of media. One important operating parameter is the gas pressure in the oxygenator fibers. The optimal pressure is a function of the number of strands of fibers used, and the pressure of the perfusing media in the ECS. For example, a bioreactor embodiment described in the Examples that had 180 Mitsubishi polypropylene fibers showed a bubble point of >2.5–3 psi. For a HPBr with 540 oxygenator fibers, the bubble point was closer to about 2 psi. As cell mass increases and cells adhere directly to the fibers, the bubble point will tend to increase.

The maximum operating pressure for gas in the HPBr should not exceed the bubble point of the oxygenator fibers in the device. The preferred operating pressure is from about 0.5 to about 1.5 psi. This range of operation avoids gas collecting in the ECS, which is injurious to cells when the device is rotated to keep cells suspended.

Table 1 illustrates the relationship between the number of oxygenator and media fibers for two types of HPBr's described in Example II (i.e., Type I and II). Two additional HPBr configurations (Type III and IV) and an OXY-1/BR110 combination are included for comparison. The tabulated information demonstrates that as the ratio of oxygenator fiber surface area to media fiber surface area increases, oxygenation efficiency also increases at the expense of the extracapillary space available for cell culture.

HPBr Type IV represents a more extreme case covered by this invention, where the annular cell culture space is within the range for a BR110 (conventional) bioreactor. The ECS of 11.8 mL is within the range expected from about 70% (maximum) fiber packing density for a BR110 or OXY-1. (The maximum space in the potted jacket with absolutely no fiber present is about 22 mL.) For the embodiment described in Example II, the oxygenator/media fiber surface area ratio range is between 0.03 to 5.5. The preferred range is between about 0.1 and about 3.1. As this data shows, the invention may be regarded as an oxygenator device within which cells are cultured and media supply is provided by a relatively few porous hollow fibers or a large porous tube, e.g., a graphite tube.

TABLE 1

Relationship Between Oxygenator and Media Supply Fibers in HPBr

| | OXY-1/ BR110 Combination | High Performance Bioreactors | | | |
|---|---|---|---|---|---|
| | | Type I | Type II | Type III | Type IV* |
| Oxygenator Fiber S.A. (ft²) | 1.0 | 0.1 | 0.3 | 0.5 | 1.1 |
| Media Fiber S.A. (ft²) | 1.5 | 0.2 | 0.2 | 0.2 | 0.2 |
| Oxy/Media Fiber Ratio | 0.7 | 0.5 | 1.5 | 2.5 | 5.5 |
| Extracapillary Space (mL) | n/a | 19.5 | 18.0 | 16.4 | 11.8 |

*Note: Based on 2000 oxygenator fibers at a maximum packing density (i.e., ~70%).

The gas composition is important in defining the efficiency of oxygenation as well as the pH in the microenvironment for cell growth created in the ECS. Illustrative data showing the effect on pH is presented in Example II. This invention permits more accurate monitoring and control of pH in the optimal range required than had been possible previously.

Provision is made in the bioreactor for an outer annular space between the outermost oxygenator fibers and the inner wall of the jacket. This space is a specially designed part of the ECS for containing cell mass. This culture space is relatively dependent of oxygenator fiber numbers, and it facilitates mixing when the bioreactor is (optimally) periodically rotated to-and-fro (by 120 degrees). Further, it facilitates sampling and harvesting of products (particularly intact viable cells, e.g., for cellular therapy applications). This space also enables microcarriers for anchorage dependent cells to be contained in the HPBr. A specific instance where this is critical is in the culture of hematopoietic stem cells for cellular therapy applications. Stem cells are grown most efficiently in the presence of anchorage dependent stromal cells (including endothelial cells). However, stem cells are anchorage independent. Therefore, stromal cells immobilized in or on microcarriers can be co-cultured with stem cells. The micro-environment thus created will facilitate the hitherto unrealized goal of long term ex-vivo expansion of stem cells. High yields and viability for cells from this cell culture space are achievable.

As noted above, periodic rotation of the bioreactor to-and-fro (about 120°) around its longitudinal axis (in the range of from about 1 to about 120 cycles per minute) provides superior cell yield and viability results as compared to static incubation.

An inner annular space may also or alternatively be provided between the annular bundle of oxygenator fibers and the central bundle of media fibers. It is designed to contain microcarriers and anchorage dependent cells (such as hepatocytes) that are cultivated at very high densities (e.g., for a bioartificial liver application). The inner annular space is accessed with a hypodermic syringe needle that passes through both the side port of the outer jacket and a port in the flow distributor plate in the device. The volume of this space decreases as oxygenator fiber number (and hence packing density) increases.

Finally, expensive growth factors and cytokines that are vital to the growth and differentiation of various cell types can be applied in relatively small quantities to the ECS to further tailor the micro-environment.

Important and unique features of the invention, both separately and in combination, include: a relatively high ratio of gas to media supply fibers in a single jacket; control of oxygenation and pH by gas composition, pressure and flow rate; relatively low fiber packing density to provide an extracapillary space for growing large cell mass and containing microcarriers; porous tubes or hollow fibers are employed to supply media and porous or non-porous hollow fibers are concentrically arranged to supply oxygenated gases, and arranged to create an inner and/or outer annular space(s) for cell culture.

Two different types of hollow fibers are used, that are made from different materials. This is represented by the examples in this invention.

One type of fiber (e.g., microporous polypropylene) is utilized where media perfusion and gas exchange in the respective bundles are achieved and controlled by regulating pressures. In applications where anchorage independent cells are being cultured at very high densities, hydrophobic fiber may be preferred so that cells grow primarily in suspension and not on the fibers.

Media supply may be provided by a single porous tube or by a bundle of hollow fibers.

Coatings may be applied to hollow fiber or tube surfaces to influence cell attachment (either positively or negatively). For example, extracellular matrix (ECM) molecules (found in connective tissue between cells in vivo) when coated onto bioreactor fibers facilitates adhesion of anchorage dependent cells like endothelial cells and Chinese hamster (CHO) cells. Other molecules containing the active amino acid sequence arginine-glycine-aspartic acid (called "RGD") found in matrix molecules also provide this benefit. For example, extracellular matrix molecules coated onto HPBr surfaces facilitate a microenvironment conducive to efficient gene transfer into hematopoietic stem cells.

Additional surface area for anchorage dependent cells is achieved by introducing microcarriers to the culture space in the ECS. Co-culturing of different cell types to gain synergistic benefit is permitted (e.g., stem cells and stroma).

A high concentration of free radicals from an enriched oxygen supply is known to impair cell growth. Addition of free radical scavengers such as sodium benzoate at relatively high concentrations (e.g., up 0.05 M sodium benzoate in DMEM) can greatly enhance metabolic performance (e.g., lower LPR/GUR), productivity and cell mass. Suitable free radical scavengers for this purpose include sodium benzoate, benzoic acid, and derivatives in which an electron-withdrawing atom or group is substituted on the aromatic ring.

PROVISION OF MICROCARRIERS

Microcarriers are small spheres with surfaces designed to achieve high yield monolayers of anchorage-dependent (or adherent) cells in culture. Microcarriers are usually suspended in culture media by gentle stirring. Six characteristics contribute to the optimum microcarrier: (1) suitable surface properties for cell attachment, spreading growth, and (for certain applications) genetic transformation; (2) density only slightly greater than the surrounding media (i.e., 1.030–1.045 g/mL); (3) narrow size distribution within the range of 100–230 μm diameter; (4) optical clarity for observing cell behavior; (5) non-toxic; and (6) some degree of compressibility to minimize cell damage when particles collide. Microcarriers may be categorized into four groups by their surface properties and applications.

| Example | Application |
|---|---|
| GROUP I: Cationic (i.e., Positively) Charged Functional Groups | |
| 1. Amino Acids | |
| e.g., poly-D-lysine | General - Bind Cells |
| 2. Charged Amino Groups | |
| e.g., Cytodex 1, by Pharmacia [N,N-diethylaminoethyl (DEAE)] | General - Bind Cells, DNA, and RNA |
| or Cytodex 2, by Pharmacia [N,N,N-trimethyl-2-hydroxyamino-propyl quaternary amino group] | General - Bind Cells, DNA and RNA |
| 3. Cationic Lipids Containing Macromolecules e.g., N-[1-92,3 dioleyloxy)-propyl]-n,n,n-trimethylammonium-chloride (DOTMA) by Life Technologies | General - Bind Cells, DNA and RNA |
| GROUP II: Neutral Functional Groups | |
| 1. Neutral Lipids | |
| e.g. dioleoyl phosphatidylethanol-amine (DOPE) by Life Technologies | General - Bind Cells |
| GROUP III: Anionic (Negatively) Charged Functional Groups | |
| 1. Nucleic Acids and Oligonucleotides e.g., Poly(dT) | Binds RNA and DNA Binds RNA containing poly(A) |
| GROUP IV: Extracellular Matrix Binding Site | |
| 1. Extracellular Matrix (ECM) Molecules e.g., Cytodex 3, by Pharmacia [collagen] | Bind Primary Cells (Others) Bind Hepatocytes (Others) |
| Others: Fibronectin Vitronectin Laminin Proteoglycans (e.g., Heparan sulfate) | Bind Primary Cells (Others) |
| 2. Arg—Gly—Asp (RGD) Containing Macromolecules e.g., (RGD) Peptides or (ECM) Cell Binding Domain Containing Macromolecule | Bind Primary Cells (Others) |

For conventional microcarrier suspension cell culture applications, the Poisson distribution equation:

$$P = \frac{e^{-\lambda} \cdot \lambda^n}{n} \quad (1)$$

is used to determine the proportion (P) of microcarriers carrying a specific number of cells (n) at various cell/microcarrier ratios (λ). The critical cell-to-microcarrier inoculation ratio necessary to obtain a negligible proportion of empty microcarriers in culture is calculated. An inoculation ratio of >7 ensures that <5% of microcarriers are unoccupied, and maximizes the use of available surface area. Inoculation ratios when microcarriers are employed in the HPBr can range from 7 to several hundred depending on the specific application. The highest inoculation ratios are used for very high density cell culture applications (e.g., bioartificial liver device). For gene transfection of adherent cells the inoculation ratio would be markedly lower.

EXAMPLE I

Two 15 day cell culture experiments were conducted with 3C11 hybridoma cell line, that secretes IgG1 monoclonal antibody in a UniSyn Cell Pharm 1000 pilot scale bioreactor system. In run 1, three UniSyn BR110 bioreactor cartridges (1.5 ft$^2$ cellulose hollow fibers) were equipped with a UniSyn OXY-1 oxygenator (1 ft$^2$ 0.2 μm pore size polyethylene oxygenator fibers) for oxygen mass transfer. In run 2, three high performance bioreactor (HPBr) equivalently sized cartridges (#1, #2, and #3) were fitted to evaluate the capacities of HPBr in 3C11 cell culture. These HPBr's all had 450 cellulose hollow fibers (with 10 kD M.W. cut-off) but #1 and #2 had different amounts of oxygenator fibers (in the form of a mat, as used in OXY-1); and, #3, 504 polyethylene oxygenator fibers.

Figure 11:
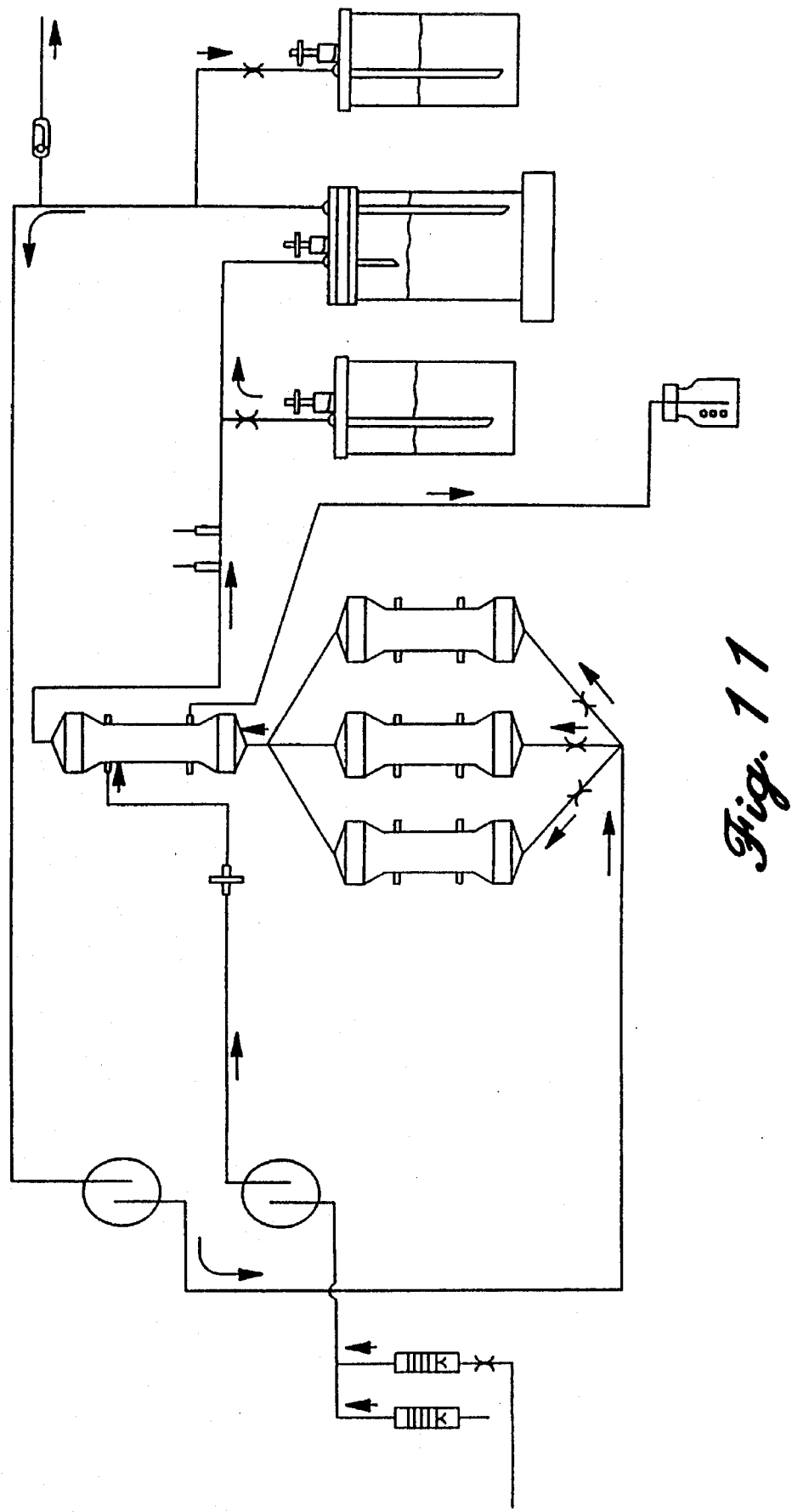
FIG. 11 depicts a first bioreactor system described in Example I.

FIG. 11 is a schematic of the flow path for three BR110 cartridges with one OXY-1 cartridges used for run 1. Media recirculation rate was established by setting the CPM of the media recirculation peristaltic pump. The mixed gas containing $CO_2$ and air was pumped through the oxygenator counter current to media recirculating in the ICS loop of the bioreactors by using the gas peristaltic pump. Calibrating pH and temperature probes were performed according to the operator's manual. To control the pH in the range of 7.0 to 7.4 in ICS media, the control unit of the Cell Pharm 1000 adjusted the $CO_2$ percentage in the mixed gas automatically.

Figure 12:
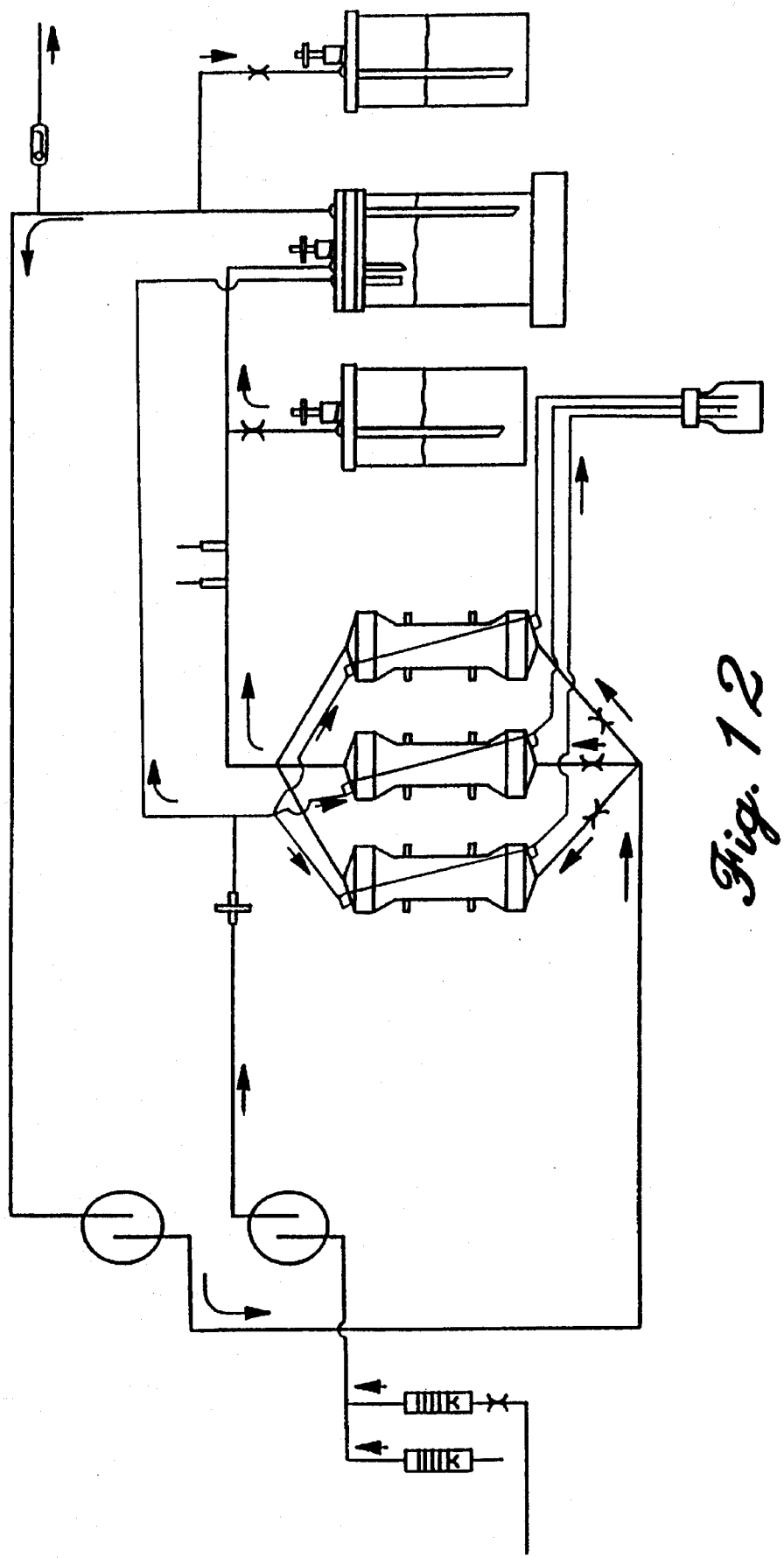
FIG. 12 depicts a second bioreactor system described in Example I.

Also, this control unit maintained the constant temperature at 37° C. FIG. 12 is a schematic of the flow path for the three HPBr cartridges in run 2. No change has been made for ICS media flow path relative to run 2. However, a modified gas flow path was designed. This involved connecting the gas mixture supply to both the three HPBr's and the media reservoir. It should be noted that this crude modification of the existing Cell Pharm 1000 did not provide optimal control of gas flow and back pressure. Connecting the gas supply with the ICS recirculation media reservoir facilitated pH control by the Cell Pharm 1000 system controller.

The entire flow path including all tubing, filters, probes, and reservoirs, renew, and waste bottles were autoclaved at 120° C. for thirty minutes on the liquid cycle. Final assembly included mounting the bioreactor cartridge into the Cell Pharm 1000 System. Contamination check and system flush were set to run for 24 hours to ensure sterility, removal of glycerine (processing aid for cellulose fibers), and allow for system stability.

Media conditions:
(i) ICS—5% fetal bovine serum (FBS) +1% penicillin/streptomycin+2% glutamine in 1000 mL DMEM;
(ii) ECS—20% FBS +1% penicillin/streptomycin +2% glutamine in 1000 mL DMEM.

Each bioreactor cartridge, including the BR110 and HPBr, was inoculated with $3\times10^8$ cells (over 90% viability) into the ECS by using two sterile, 10 mL syringes with attached 18 gauge needles. One syringe contained 5 mL of ECS media and the cells. The second syringe was empty and used to collect the media displaced during the inoculation.

Product harvest was accomplished in a manner similar to the inoculation procedure. Harvesting was typically done three times a week and 10 mL/each, and the standard operating procedure for this Cell Pharm 1000 System was followed for maintaining cell culture daily.

Process parameters in the cell culture systems were set up to monitor glucose uptake, lactate production, $NH_3$ production, MAb production and perfusion rate of ICS media. Since one cannot directly estimate the cell mass present in the hollow fiber bioreactor at any given time, the MAb production may be regarded as a means for measuring the effect of oxygen mass transfer within the two types of bioreactors in runs 1 and 2. MAb concentration in the harvest was analyzed by using radial immunodiffusion assay; glucose, lactate, and $NH_3$ sampled from the ICS of the bioreactor were analyzed by using a Kodak Ektachem Analyzer. The perfusion rate was determined by measuring the media level of renew bottles. Initial perfusion rate was started at 240 mL/day and was increased step by step and maximized up to 1000 mL/day until the end of the runs according to either the glucose concentration (when it fell as low as 1.5 g/L) or lactate concentration (when it reached as high as 20 mM).

Figure 13:
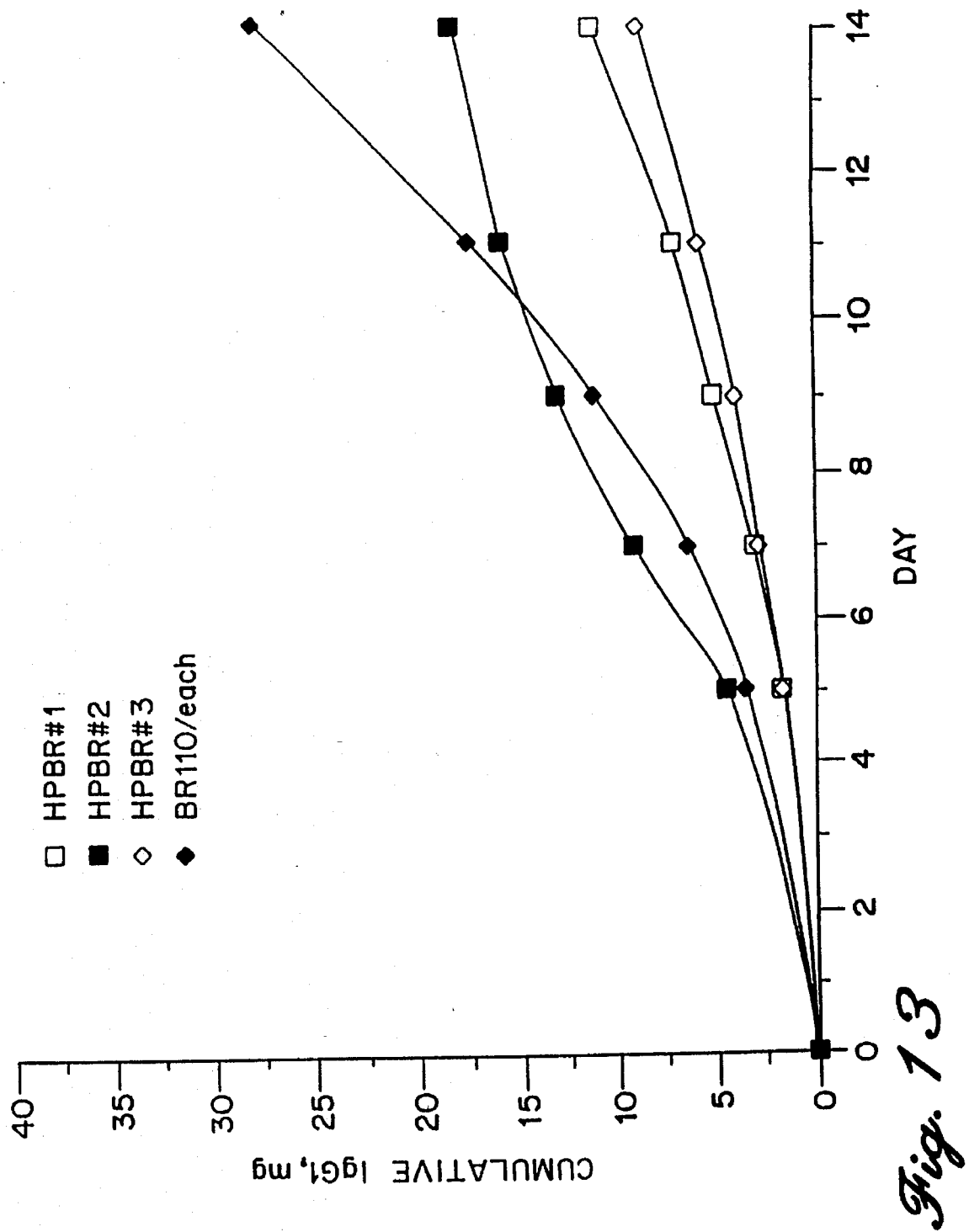
FIG. 13 presents the results of Example I.

Cumulative MAb production in each HPBr cartridge (run 2) for 3C11 cells, are compared to that in each BR110 (run 1) are shown in FIG. 13. The ratio of lactate production rate to glucose consumption rate was developed as an indicator to evaluate the effect of oxygen mass transfer. This ratio was significantly lower in run 2 (shown in FIG. 4) compared to run 1. These results suggest that the oxygenator fibers in HPBr cartridges help to reduce the resistance of oxygen mass transfer to the grow cells. This was especially true for the HPBr cartridge with the Mitsubishi oxygenator fibers that gave higher MAb production levels than those in the other two HPBr's which have polyethylene oxygenator fibers. It was assumed that the relatively high dissolved oxygen concentration in the ECS lets cells grow more efficiently.

EXAMPLE II

A 25 day cell culture experiment (run 1) was conducted with 3C11 hybridoma cell line, that secretes IgG1 monoclonal antibody. A test system was designed to evaluate the performance of three HPBr cartridges under controlled conditions. As a reference, a UniSyn Micro Mouse BR110 small scale bioreactor with a UniSyn OXY-1 oxygenator was employed in run 2. Run 3 consisted of a UniSyn Micro Mouse BR110 small scale bioreactor with a silicone tubing for oxygen mass transfer by diffusion.

Figure 14:
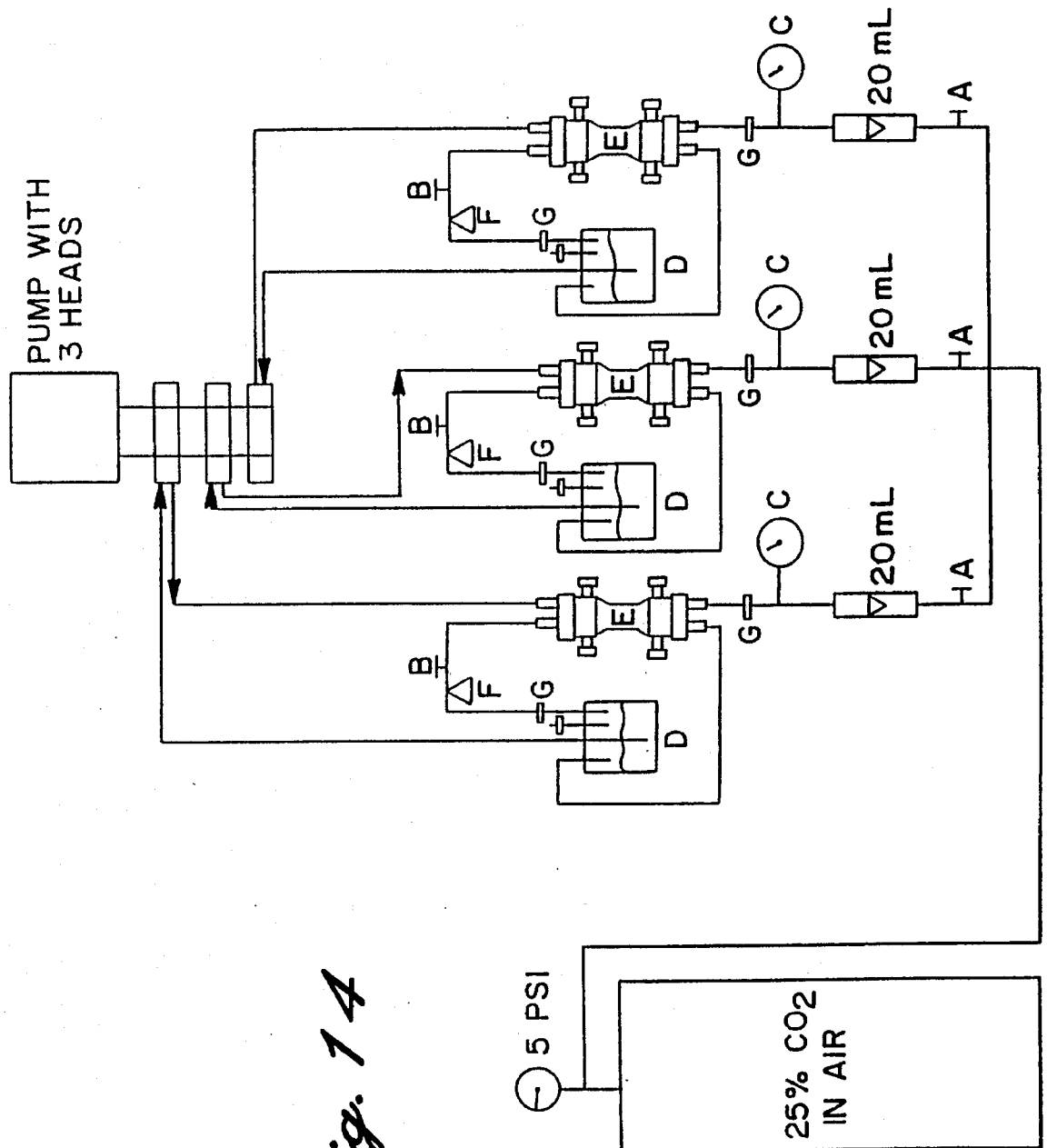
FIG. 14 depicts the reactor system described in Example II.

Run 1 used the test system that was designed to operate HPBr's with the media flow path and the gas flow rate and pressure manually controlled (see FIG. 14). A peristaltic pump assembly was used with three pump heads to provide the same media recirculation flow through each HPBr at a flow rate of 100 mL/min. Temperature in the ECS of each HPBr was controlled at 37° C. by immersing the three media reservoirs in a thermostatically controlled recirculating water bath. The ICS media pH was controlled in the range from 7.00–7.30 by aerating the space above the media in the reservoir with $CO_2$ in 75% to 85% air. This gas mix was also used to supply gas to the three HPBr cartridges with a constant flow rate of 38 mL (stp/min) and back pressure of 1.5 psi.

The three HPBr cartridges each had 450 cellulose hollow fibers for supplying media to the cells by perfusion. Both HPBr #1 and #2 had 180 Mitsubishi oxygenator fibers. The number of Mitsubishi oxygenator fibers in HPBr #3 was three times higher than that in #1 and #2. For run 1, the contamination check and system flush were performed according to the instructions found in the Micro Mouse operating manual.

Run 2 was assembled in an oven for maintaining a constant temperature (37°). Premixed air and $CO_2$ was passed through the OXY-1 oxygenator at a rate of about 70 mL(stp)/min counter current to the direction of the loop recirculating media in the ICS of the BR110 bioreactor. To control pH within the range from 7.0 to 7.4, the ratio of $CO_2$ to air was adjusted by using valves on two gas flow meters.

Run 3 was mounted in a $CO_2$ incubator for maintaining a constant temperature (37° C.) and constant pH (from 7.0 to 7.2) in the ICS media was established by setting the ratio of 7% $CO_2$ to 93% air in incubator.

Media conditions:

(i) ICS—5% FBS+1% penicillin/streptomycin+2% glutamine in 1000 mL DMEM;

(ii) ECS—20% FBS+1% penicillin/streptomycin+2% glutamine in 1000 mL DMEM.

$3 \times 10^8$ cells (91% viability) were inoculated in the ECS by using two sterile, 10 mL syringes with 18 gauge needles. One syringe contained 5 mL of ES media and cells. The second syringe was empty and used to collect the media displaced during the inoculation. Both run 2 and 3 were inoculated with $4 \times 10^8$ cells (95% viability) in the ECS using the method illustrated above. The standard operating procedure for run 2 and 3 was followed for maintaining cell culture daily. For run 1, daily adjustment of back pressure and gas flow rate, sampling from each ICS media and harvesting from ECS of each cartridge were carried out.

Process parameters in the cell culture systems were set up to monitor glucose uptake, lactate and $NH_3$ production and MAb production. Cumulative MAb production was monitored to determine the effect of different oxygen mass transfer methods exemplified in runs 1–3.

ICS media for the bioreactors was replaced with fresh media when either the glucose concentration fell below 2.0 g/L or lactate concentration was higher than 20 raM. For run 2 and run 3, harvesting of MAb from the ECS of the bioreactor was done three times weekly and a volume of 10 mL/each (as defined by the Micro Mouse protocol). MAb production was analyzed by using radial immunodiffusion assay; and glucose, lactate, $NH_3$ concentration in harvesting of the ECS of HPBr's were also analyzed. The difference between the levels for these cell metabolites found in the ICS and the ECS of HPBr were noted.

Figure 15:
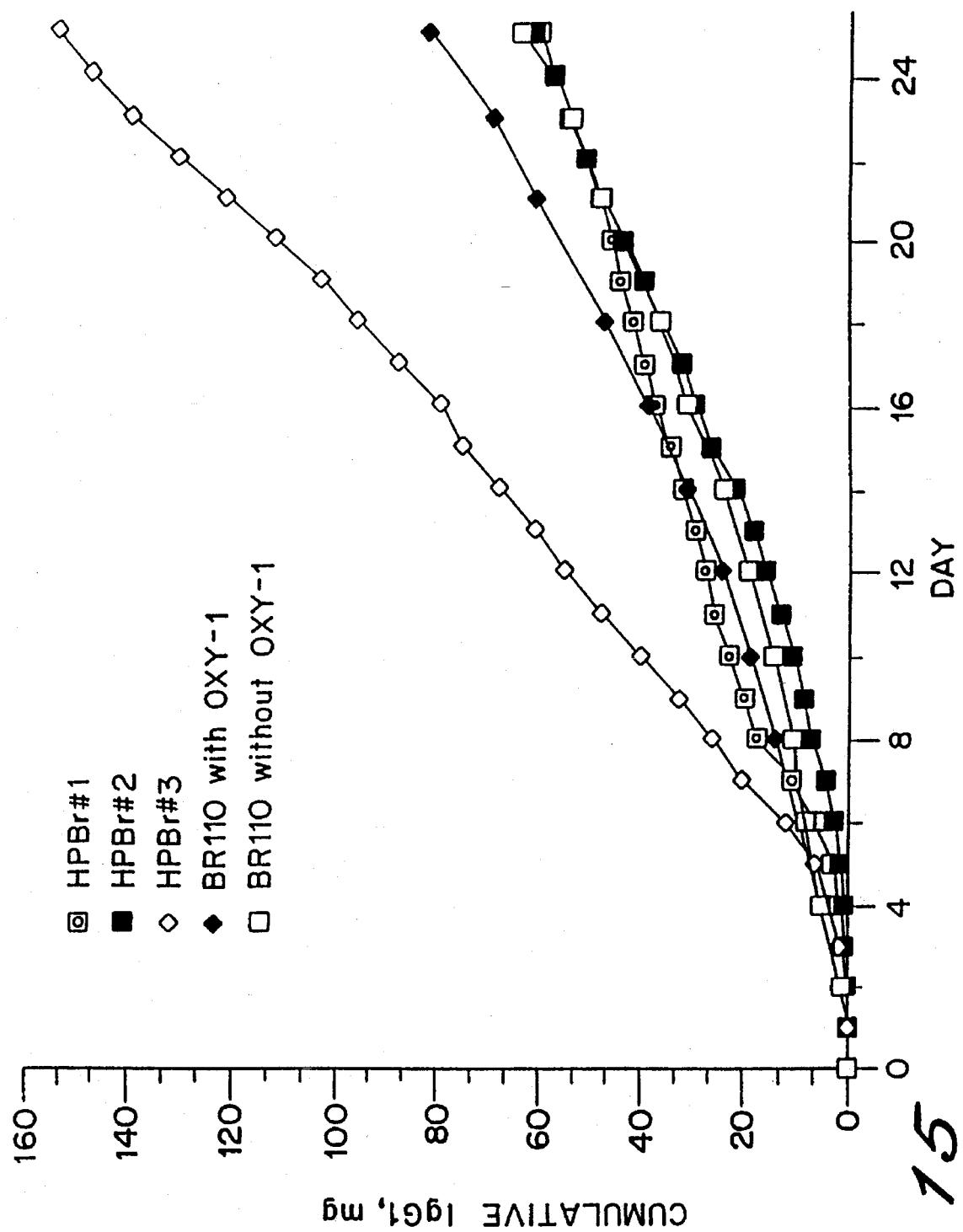
FIG. 15 presents the results of Example II.

FIG. 15 shows the cumulative IgG1 produced in each HPBr cartridge and in runs 2 and 3. HPBr #3 appeared to be superior in MAb production compared with HPBr #1 and #2. A similar conclusion was drawn when the HPBr was also compared with BR110 bioreactor in run 2 and run 3. This suggests that the increase of oxygenator fibers in HPBr can significantly enhance cell growth and MAb production due to the increased oxygen supply. Also the ratio of LPR to CUR was calculated for HPBr #3 and found to be significantly lower than other bioreactors. This signifies more efficient utilization of glucose in the presence of increased oxygen in the ECS.

Figure 16:
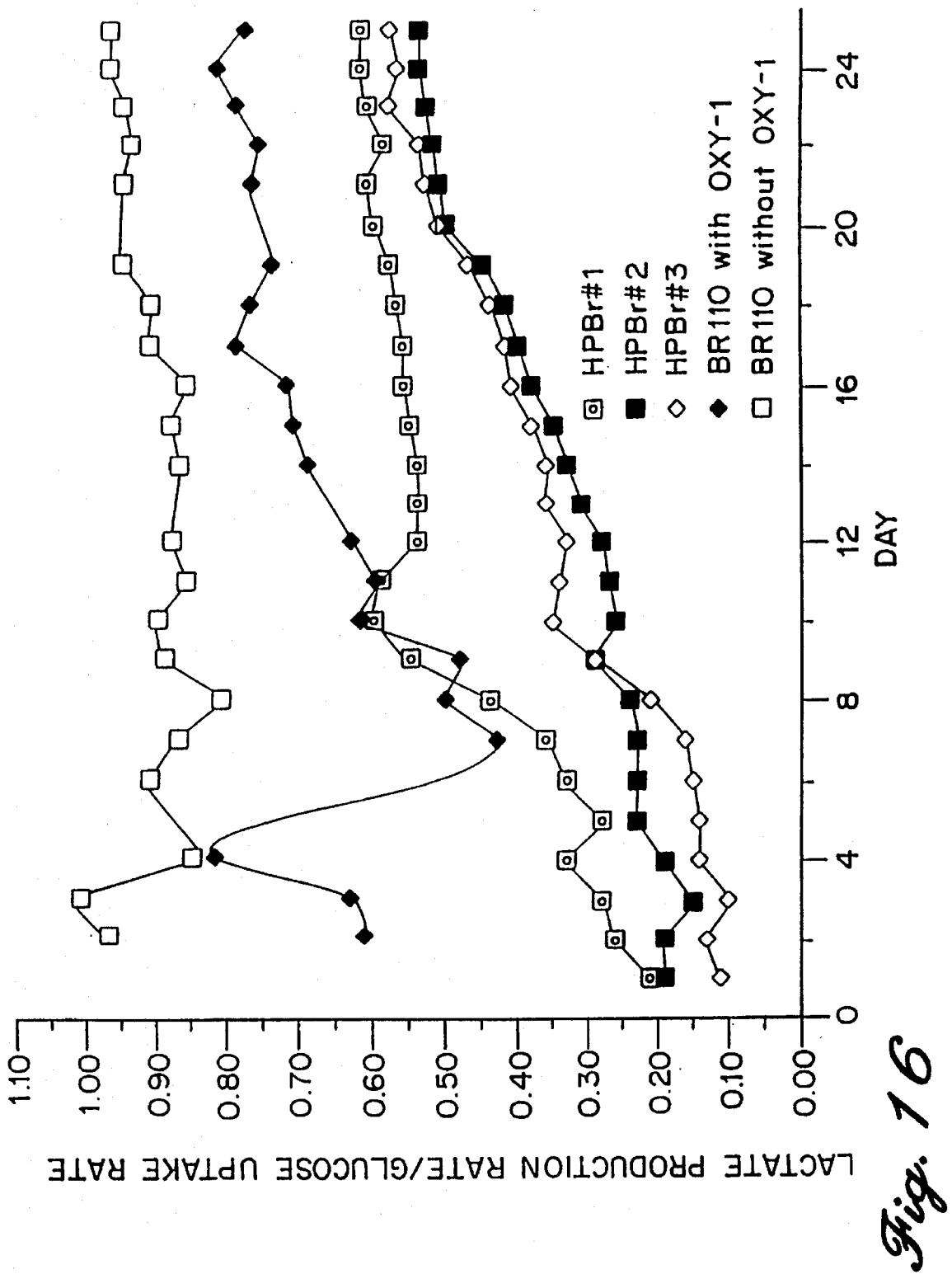
FIG. 16 compares the ratio of lactate production rate/ glucose utilization rate for various bioreactors.

FIG. 16 compares the ratio of lactate production rate/glucose utilization rate for various bioreactors. The lowest ratio was shown by HPBr devices, and these low values remain below that of the conventional bioreactors and oxygenation methods for prolonged cell culture runs. Ideally, the ratio should be as close to zero as possible throughout the cell culture run, signifying optimal metabolic utilization of glucose.

Table 2 is a comparison of bioreactor and oxygenator properties. It also contains the relative antibody productivity of bioreactor/oxygenator combination as a function of their physical properties. In this embodiment, as the number (or surface area) of oxygenator fibers increase, and the ratio of oxygenator to media fiber surface areas increase, bioreactor productivity also increases.

TABLE 2

| Property | BR1100 (Bioreactor) | OXY-1 (Oxygenator) | HPBr Type I Media | HPBr Type I Oxygenator | HPBr Type II Media | HPBr Type II Oxygenator | HPBr Type III Media | HPBr Type III Oxygenator |
|---|---|---|---|---|---|---|---|---|
| Material | Cellulose | Polyethylene | Cellulose | Polypropylene | Cellulose | Polypropylene | Cellulose | Polypropylene |
| MWc or Pore Size | 10 kD | 0.2 μm | 10 kD | 0.2 μm | 10 kD | 0.2 μm | 10 kD | 0.2 μm |
| Surface Area (O.D.) ft² | 1.5 | 1.0 | 0.2 | 0.1 | 0.2 | 0.3 | 0.2 | 0.5 |
| Number of Fibers | 3150 | 1684 | 450 | 180 | 450 | 540 | 450 | 900* |
| Permeability of Media Fibers (mL/hr. mmHg) | 0.2 | n/a | $2.8 \times 10^{-2}$ | n/a | $2.8 \times 10^{-2}$ | n/a | $2.8 \times 10^{-2}$ | n/a |
| Typical IgG₁ Productivity (mg) for 3C11 Hybridoma after 14 days of culture (batch run) | 23 | | 32, 22 | | 68 | | Data not available at this time | |

*Note: Maximum number of oxygenator fibers possible in this embodiment of HPBr is about 2000 (i.e., 1.1 ft²). This assumes a packaging density of 70%, which is in the range that is typical of conventional hollow fibers devices in general.

Figure 17:
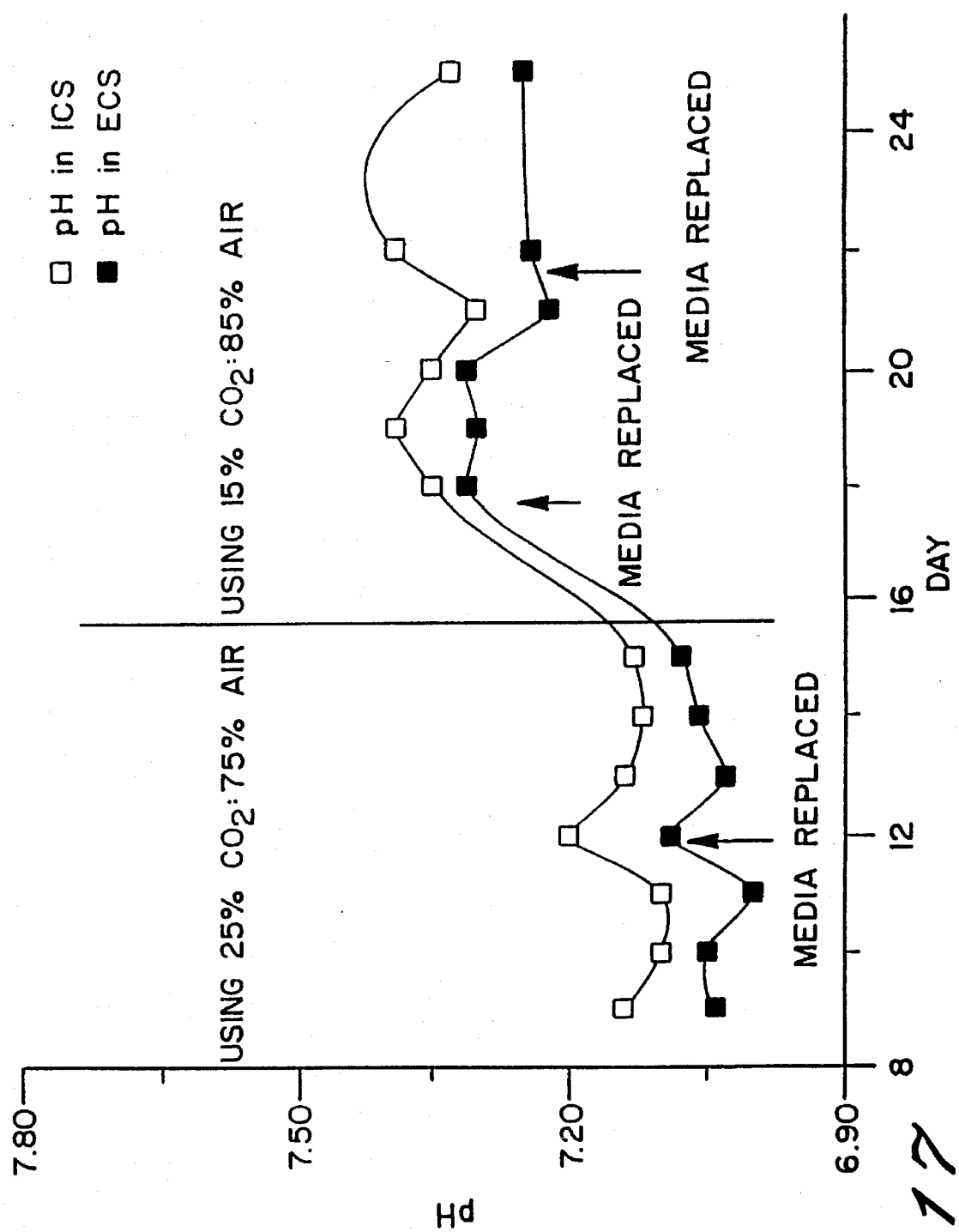
FIG. 17 illustrate the level of pH control achievable with the HPBr.

FIG. 17 illustrates the level of pH control achievable with the HPBr. The particular data depicted is for HPBr #3. pH control regulates biomass production vs. MAb production. Lower pH, e.g., 7.0, tends to encourage cells to remain in the exponential growth phase to produce high biomass. Higher pH, e.g., 7.4, tends to encourage cells to remain in the steady state phase and therefore exhibit higher productivity.

EXAMPLE III

The propagation of 3C11 hybridoma cells was carded out in high performance hollow fiber bioreactors (HPBr) with different numbers of oxygenator fibers for 30 day antibody production runs. Table 3 summarizes the physical properties of these HPBr's. The IgG1 antibody product in the cell culture supernatant was quantitated by radial immunodiffusion (RID) assay.

High performance bioreactor (HPBr) cartridges were assembled aseptically to the test system (as shown in FIG. 14). A peristaltic pump assembly was used to provide the ICS media recirculation flow through each HPBr at a flow rate of 130 mL/min. The temperature in the ECS of each HPBr was controlled at 37° C. by immersing the ICS media reservoir in a thermostatically controlled recirculating water bath. The ICS media pH was controlled in the range from 7.00–7.40 by aerating the space above the media in the reservoir with premixed gas with 10% $CO_2$ in air. This gas was also used to supply oxygen to the HPBr cartridge with a constant flow rate of 63.2 mL(stp)/min, and back pressure of 1.0–1.5 psi.

The second syringe was empty and used to collect the media displaced during the inoculation.

The gas back pressure was maintained in the range from 1.0 to 1.5 psi to prevent displacement of media from the ECS due to the pressure of gas in the lumens of oxygenator fibers. Since the dry gas which passes through the oxygenator fibers sweeps out water that condenses in the ECS, a liquid trap was used downstream of the HPBr. The liquid trap was cleaned daily. A cell culture protocol was established to

TABLE 3

| | Range of Structural Properties for HPBr | | | | | | | | |
|---|---|---|---|---|---|---|---|---|---|
| Item | Run 1 | Run 2 | Run 3 | Run 4 | Run 5 | Run 6 | Run 7 | Run 8 | Run 9 |
| Number of Media Fibers | 450 | 450 | 450 | 450 | 450 | 450 | 450 | 450 | 450 |
| Material of Media Fibers | Cellulose | Cellulose | Cellulose | Cellulose | Cellulose | Cellulose | Cellulose | Cellulose | Cellulose |
| M.W. Cut-Off | 10K | 10K | 10K | 10K | 10K | 10K | 10K | 10K | 10K |
| Media Fiber Surface Area (O.D.), sq. ft. | 0.21 | 0.21 | 0.21 | 0.21 | 0.21 | 0.21 | 0.21 | 0.21 | 0.21 |
| Number of OXY Fibers | 180 | 360 | 540 | 720 | 900 | 1080 | 1260 | 1620 | 1960 |
| Material of OXY Fibers | Polypropylene | Polypropylene | Polypropylene | Polypropylene | Polypropylene | Polypropylene | Polypropylene | Polypropylene | Polypropylene |
| Average Pore Size (μm) | 0.2 | 0.2 | 0.2 | 0.2 | 0.2 | 0.2 | 0.2 | 0.2 | 0.2 |
| OXY Fiber Surface Area (O.D.), sq. ft. | 0.11 | 0.22 | 0.33 | 0.44 | 0.55 | 0.66 | 0.77 | 0.99 | 1.21 |
| Surface Area Ratio: OXY/Media Fiber | 0.52 | 1.05 | 1.57 | 2.1 | 2.62 | 3.14 | 3.67 | 4.69 | 5.76 |
| Packing Density | 0.15 | 0.21 | 0.26 | 0.31 | 0.36 | 0.42 | 0.47 | 0.58 | 0.68 |
| ECS (mL) | 18.8 | 18 | 17.3 | 16.5 | 15.7 | 15 | 14.2 | 12.7 | 11.2 |
| Category of HPBr | Ia | | | Ib | | II | | III | |

HPBr cartridge configurations used are shown in Table 3. Each HPBr cartridge had 450 cellulose media fibers for supplying nutrient to cells by perfusion into the ECS. The oxygenating fiber membranes enable oxygen to diffuse into the ECS of HPBr cartridge to support cell growth.

Media Conditions:

ICS: 5% fetal bovine serum (FBS)+4 mM glutamine+100 k unit penicillin/100 mg streptomycin in 1000 mL DMEM (Dulbecco's Modified Eagle's high glucose (4.5 g/L) basal medium);

YECS: 20% FBS+4 mM glutamine +100 k unit penicillin/100 mg streptomycin in 1000 mL DMEM.

An inoculum containing $5 \times 10^8$ cells (over 90% viability) was syringed into the ECS of the HPBr cartridge by using two sterile, 10 mL syringes with 22 gauge needles after the ECS of the HPBr cartridge was flushed by 20 mL ECS media. One syringe contained 5 mL ECS media and cells.

monitor the glucose uptake and the production rates for lactate, $NH_3$, and antibody. Samples from ICS media of the HPBr cartridge were withdrawn daily for off line glucose, lactate and $NH_3$ analysis by using Kodak Ektachem analyzer. Harvesting of antibody from ECS of the HPBr cartridge was started ~24 hours after inoculation and continued daily thereafter, with a volume of 10 mL/day for bioreactor. The media used in ICS of the HPBr was replace by fresh media when either the glucose concentration fell below 1.5 g/L or lactate concentration was higher than 20 mM in the media. Since one cannot directly estimate the cell growth with time in the hollow fiber bioreactor, the glucose uptake rate (GUR) and lactate production rate (LPR) can be regarded as an effective metabolic signature. The LPR/GUR values were calculated to provide fundamental information about the physiological state of the cells in culture.

TABLE 4

| | Cell Growth and MAb Production in HPBr Cartridges with Different Number of Oxygenating Fibers | | | | | | | | |
|---|---|---|---|---|---|---|---|---|---|
| Item | 1 | 2 | 3 | 4 | 5 | 6 | 7 | 8 | 9 |
| Number of OXY/Media Fibers | 180/450 | 360/450 | 540/450 | 720/450 | 900/450 | 1080/450 | 1260/450 | 1620/450 | 1980/450 |
| ECS of HPBr (mL) | 18.8 | 18.0 | 17.3 | 16.5 | 15.7 | 15.0 | 14.2 | 12.7 | 11.2 |
| IgGl Production (mg) | 114.7 | 155.5 | 198.8 | 244.7 | 252.3 | 231.7 | 242.0 | 134.2 | 142.4 |
| Cell Inoculation (Viability > 90%) | $5 \times 10^8$ | $5 \times 10^8$ | $5 \times 10^8$ | $5 \times 10^8$ | $5 \times 10^8$ | $5 \times 10^8$ | $5 \times 10^8$ | $5 \times 10^8$ | $5 \times 10^8$ |
| Fold Increase of Cell Mass | 21.8 | 32.0 | 16.8 | 11.4 | 4.2 | 3.7 | 4.6 | 4.6 | 3.7 |
| Average GUR (mg/h) | 26.4 | 24.1 | 27.0 | 27.8 | 28.2 | 20.4 | 21.6 | 18.4 | 16.2 |
| Average LPR/GUR | 0.77 | 0.75 | 0.65 | 0.64 | 0.69 | 0.65 | 0.64 | 0.62 | 0.73 |

Figure 18:
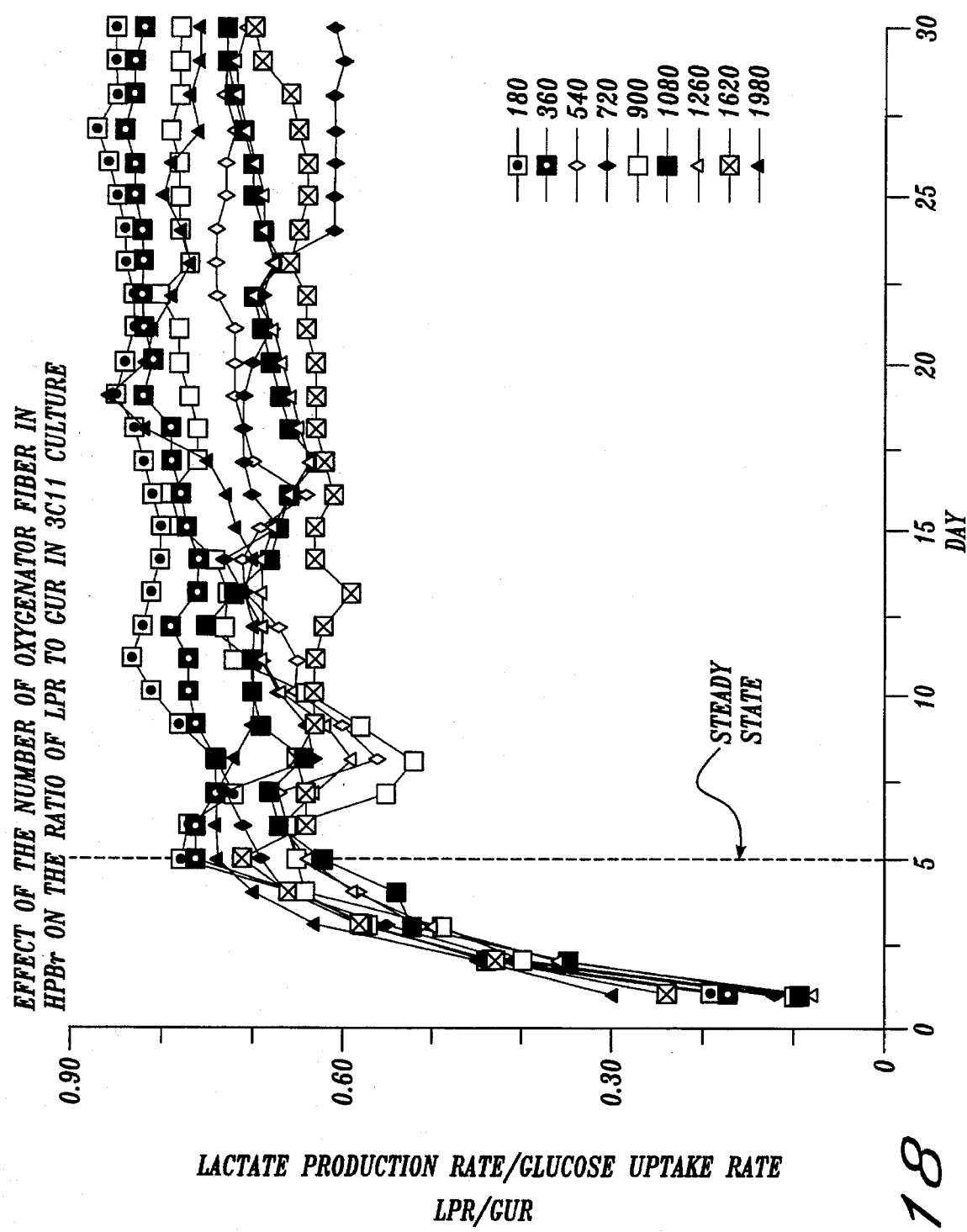
FIG. 18 depicts metabolic signature (LPR/GUR) for various bioreactor configurations.

Table 4 summarizes key data derived from this study. For example it shows the cumulative IgG1 produced in each HPBr cartridge in 30 days. IgG1 production appears to reach an optimal plateau with the HPBr containing oxygenator fibers ranging between 720 to 1620. FIG. 18 and Table 4 show the ratio of lactate production rate (LPR) to glucose uptake rate (GUR), which serves as a metabolic signature. The results indicate that cells produced less lactate when the number of oxygenator fibers in HPBr cartridge was increased. The average LPR/GUR values for HPBr (determined only after steady state is achieved, i.e., day 5), were $\leq 0.80$.

Figure 19:
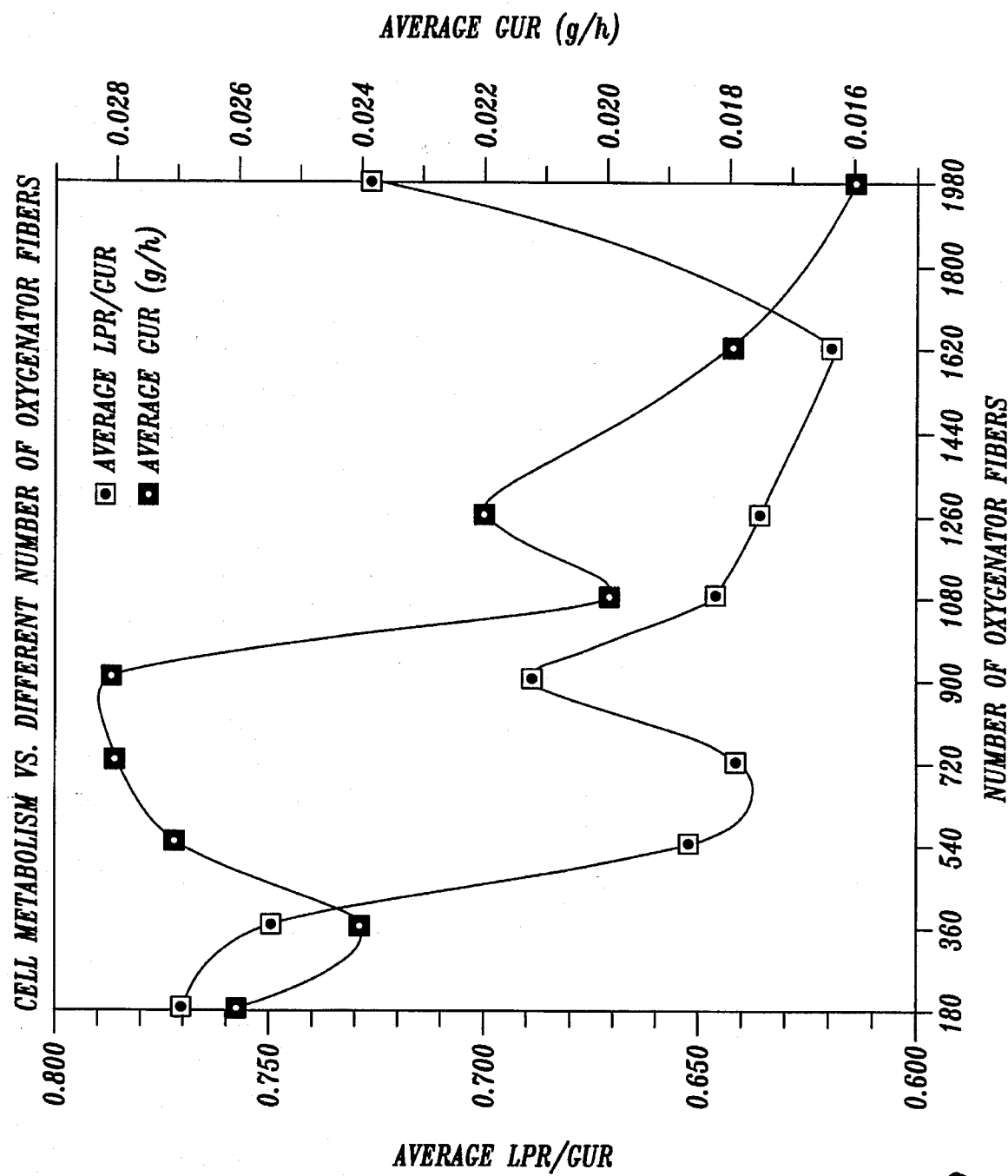
FIG. 19 compares cell metabolism for different numbers of oxygenator fiber bioreactors.
Figure 20:
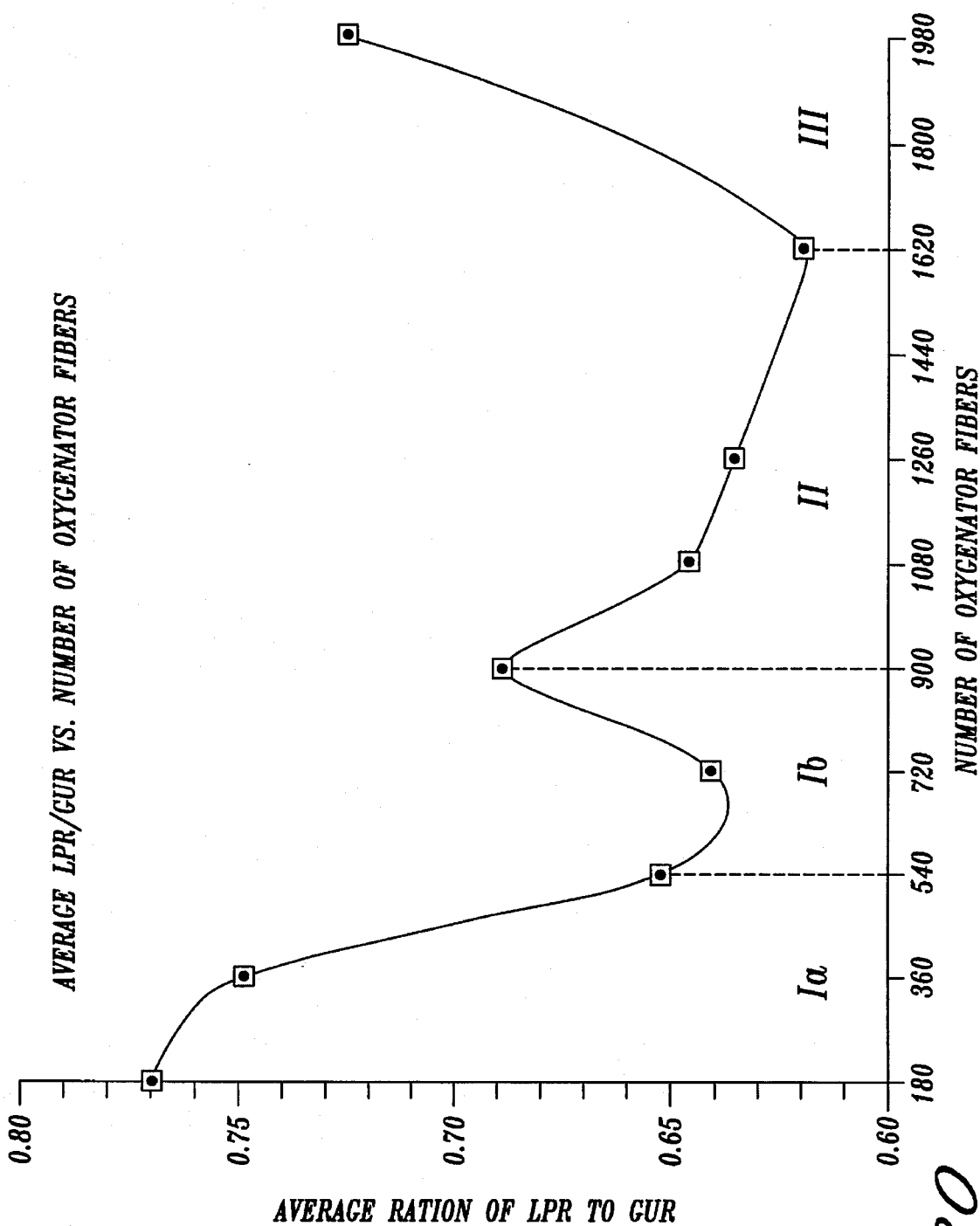
FIG. 20 shows the categorizing of HPBr's based on LPR/GUR values for different oxygenator fiber bioreactors.

FIGS. 19 and 20 depict the metabolic signatures for the variously configured bioreactors and how the GUR, LPK and LPR/GUR values can be used to classify these bioreactors for optimal use into three categories:

(i) Range I—optimally useful for cell expansion and harvesting.
   Highly efficient metabolite production, with consistently high levels of glycosylation.
   Culturing adherent cells on microcarriers.
(ii) Range II—Highly efficient metabolite production, with consistently high levels of glycosylation.
   Extracorporeal devices (e.g., bioartificial liver), for treating metabolic diseases and the like.
(iii) Range III—Relatively low efficiency metabolite production.

EXAMPLE IV 30 day cell culture experiments were carried out with high performance bioreactors employing different concentrations of sodium benzoate in the ICS media to serve as a free radical scavenger.

These bioreactors were assembled and operated as described in Example III. The concentration range for sodium benzoate in this study was: 0, 0.0001, 0.001, 0.01, and 0.1 M. Each HPBr cartridge had 450 cellulose media fibers for supplying nutrient to cells, and 540 polypropylene oxygenator fibers for oxygen mass transfer into the media in ECS of the HPBr cartridge.

Media Conditions:
Run 1 (control):
  ICS: 5% fetal bovine serum (FBS)+4 mM glutamine+100 k unit penicillin/100 mg streptomycin in 1000 mL DMEM (Dulbecco's Modified Eaglep's high glucose (4.5 g/L) basal medium).
  ECS: 20% FBS +4 mM glutamine+100 k unit penicillin/100 mg streptomycin in 1000 mL DMEM.
Run 2:
  ICS: 40 µl of concentrated sodium benzoate solution with a concentration of 0.36 g/mL in PBS+media which was the same as that used for run 1.
  ECS: The same as that used for run 1.
Run 3:
  ICS: 400 µl of concentrated sodium benzoate solution with a concentration of 0.36 g/mL in PBS+media which was the same as that used for run 1.
  ECS: The same as that used for run 1.
Run 4:
  ICS: 4 mL of concentrated sodium benzoate solution with a concentration of 0.36 g/mL in PBS+media which was the same as that used for run 1.
  ECS: The same as that used for run 1.
Run 5:
  ICS: 40 mL of concentrated sodium benzoate solution with a concentration of 0.36 g/mL in PBS+media which was the same as that used for run 1.
  ECS: The same as that used for run 1.

An inoculum containing $5\times10^8$ viable cells (over 90% viability) was introduced into each bioreactor.

TABLE 5

Effect of free radical scavenger in ICS media on cell growth/IgG1 production in HPBr for 30 day cell culture runs

| Item | High Performance Bioreactor Cartridges | | | | |
|---|---|---|---|---|---|
| | 1 | 2 | 3 | 4 | 5 |
| Material of Media Fiber | Cellulose | Cellulose | Cellulose | Cellulose | Cellulose |
| Number of Media Fiber | 450 | 450 | 450 | 450 | 450 |
| Material of Oxygenator Fiber | Polypropylene | Polypropylene | Polypropylene | Polypropylene | Polypropylene |
| Number of Oxygenator Fibers | 540 | 540 | 540 | 540 | 540 |
| Sodium Benzoate* Added | 0.0M | 0.0001M | 0.001M | 0.01M | 0.1M |
| pH in ICS Media | 7.42 | 7.41 | 7.41 | 7.5 | 7.66 |
| Cumulative IgG1 | 228.4 mg | 184.3 mg | 261.6 mg | 338.1 mg | No production |
| Cell Recovery from ECS | $8.4 \times 10^9$ | $9.5 \times 10^9$ | $1.2 \times 10^{10}$ | $1.1 \times 10^{10}$ | $<10^8$ |

*Sodium benzoate (0.36 g/mL) in PBS, pH = 8.03.

Table 5 lists HPBr performance with respect to cell growth and antibody production where different amounts of sodium benzoate was added to the ICS media. The maximum antibody production was obtained in run 4 with cumulative 338.1 mg IgG1, which was a 1.5 fold increase in viable cells (after 30 days) compared with the control run (run 1). When sodium benzoate concentration was increased up to 0.1 M, no cell growth was observed; thus IgG1 production could not be measured.

Table 5 summarizes the main features of the HPBr's employed in these studies and shows the increase of cell mass in the ECS for each cartridge after the run. The greatest increase in the number of cells was $1.2\times10^{10}$ in run 3, which represents a 24 fold increase based on the cell inoculum ($5\times10^8$ cells/each). The highest cumulative IgG1 production in 30 days was achieved in run 4 with 0.01 M sodium benzoate. However, as sodium benzoate solution has a pH of 8.2, at 0.01 M the pH exceeded the typical value for these cell culture conditions. Further, at 0.1 M sodium benzoate cell growth was impaired.

EXAMPLE V

Three high performance bioreactors with different media supply fiber/tube configurations were evaluated. Table 6 shows the distinguishing features for each bioreactor configuration. 3C11 hybfidoma was cultured for 30 to 33 days to produce IgG1 antibody. Standard ICS and ECS media compositions were employed, and the experimental procedures conducted in an identical manner to that outlined in Example III, run 1. However, there were two important deviations from this procedure: (1) the use of a "priming step" (i.e., apply a vacuum to the ECS via an empty syringe) to wet the pores of the media fibers/tube for runs 1 and 3; (2) the higher media recirculation rate for runs 1 and 2 due to fiber/tube ID. This materially affected (i.e., lowered) back pressure in the oxygenator fiber relative to that in Example III, run 1. Similarly, with the hydrophilic fibers (0.2 μm pore size) in run 2, substantial ECS perfusion was achieved under these conditions. However, in runs 1 and 3 with more hydrophobic media supply fibers/tube, much lower ECS perfusion was exhibited under the prevailing conditions.

Results are shown in Table 6. IgG1 product passed from the ECS to the ICS for run 2 (only), due to the large (0.2 μm) pores and high perfusive (or diffusive) flow between the two relative to runs 1 and 3.

TABLE 6

Configuration and Performance Properties for HPBr With Different Media Fiber/Tube

| Item | Run 1 | Run 2 | Run 3 |
| --- | --- | --- | --- |
| Media fiber | Graphite/ Ceramic Tube (Rhône Poulenc) | Mixed Cellulose Ester (Microgon) | Polypropylene (Mitsubishi) |
| No. of fiber/tube | 1 | 18 | 240 |
| ID (μm) | 5500 | 1000 | 250 |
| Pore size, μm (Average) | 0.14 | 0.20 | 0.20 |
| Surface area O.D. (ft$^2$) | 0.019 | 0.040 | 0.14 |
| Media recirculation (mL/min) | 150 | 150 | 130 |
| No. oxygenator fibers | 216 | 180 | 180 |
| Membrane material | polypropylene (Mitsubishi) | polypropylene (Mitsubishi) | polypropylene (Mitsubishi) |
| Average pore size (μm) | 0.2 | 0.2 | 0.2 |
| Surface area O.D. (ft$^2$) | 0.12 | 0.10 | 0.10 |
| Gas flow rate (mL STD/min) | 63.2 | 63.2 | 63.2 |
| Back pressure (psi) | 0.5 | 0.5 | 1.0 |
| Total ECS (mL) | 16.0 | 19.7 | 19.2 |
| Duration of run (days) | 33 | 33 | 30 |
| Cumulative IgG1 production (mg)- ICS plus ECS | 55.5 | 147.6 | 57.2 |

EXAMPLE VI

A series of high performance bioreactors with the (450 10 kD cellulose/540 0.2 μm polypropylene hollow fiber) configuration were used in 30 day cell culture runs with 3C11 hybridoma. Gas composition to oxygenator fibers was varied to evaluate the effect of oxygen composition (Table 7).

TABLE 7

Gas Composition Supplied to Oxygenator Fibers for HPBr

| | Gas Composition (%) | | | |
| --- | --- | --- | --- | --- |
| Run | O$_2$ | CO$_2$ | N$_2$ | Other |
| 1 | 10 | 10 | 80 | |
| 2 | 25 | 10 | 65 | |
| 3 | 50 | 10 | 40 | |
| 4 | 75 | 10 | 15 | |
| 5 | 90 | 10 | 0 | |
| 6 | 90 | 10 | 0 | 0.001M Sodium benzoate in ICS media |

All media compositions, experimental and analytical procedures were identical to that employed in Example III for run 3. In addition, samples from the ECS were analyzed for dissolved oxygen (DO) composition.

Figure 21:
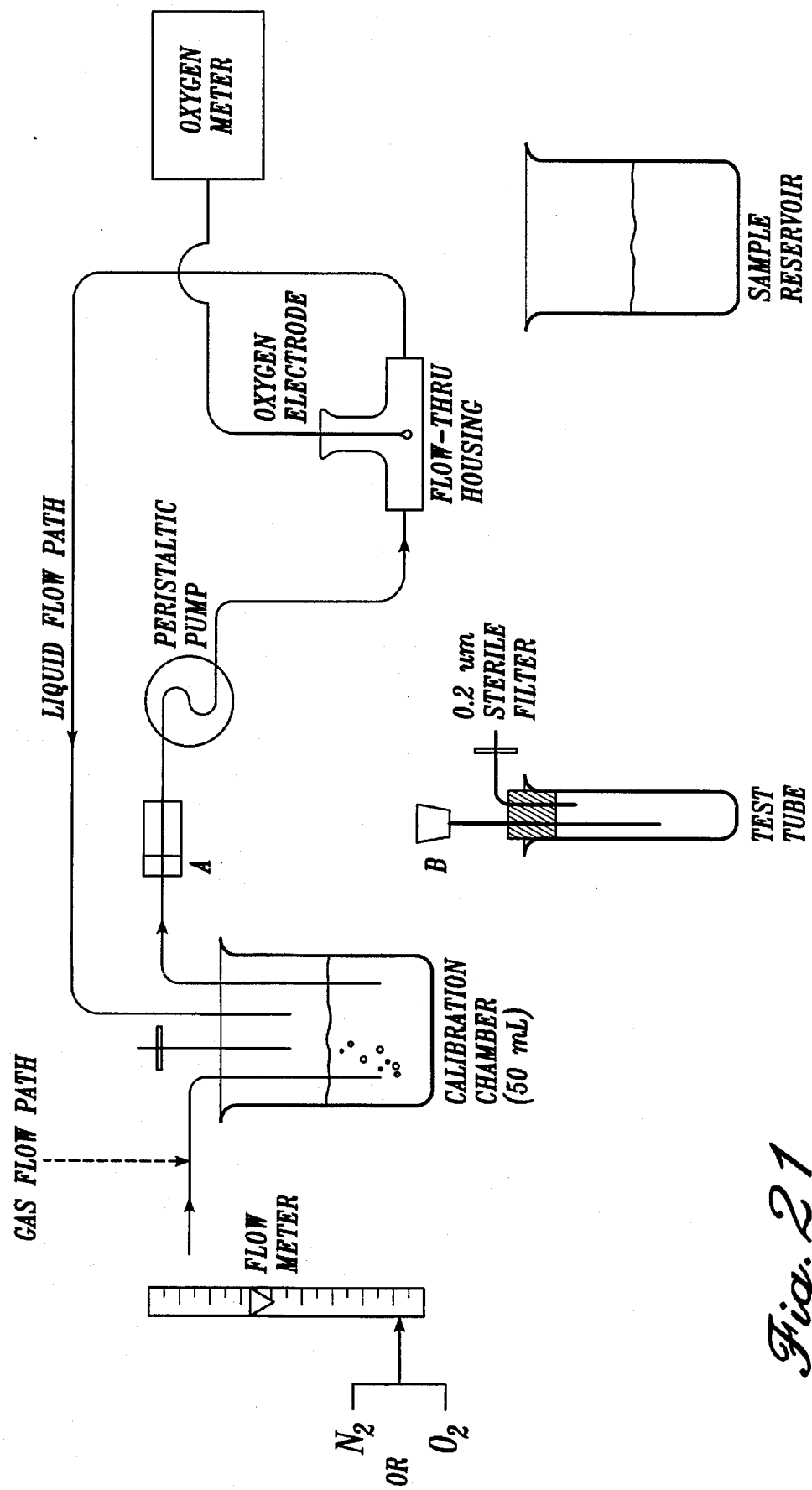
FIG. 21 depicts a test system for determining dissolved oxygen.

The test system (FIG. 21) and protocol for determining dissolved oxygen are described below.

Procedure for determination of dissolved oxygen

1. Electrode Assembly and Preparation
   a) The oxygen electrode and meter (model 8-730 and OM-4, respectively) was inserted onto the flow-thru housing according to the operating instructions provided by Microelectrodes, Inc., Londondery, N.H.
   b) The flow-thru housing was connected to the liquid flowpath, which consisted of a 50 mL calibration chamber and a peristaltic pump to maintain the flow rate.
   c) Pure $N_2$ and pure $O_2$ cylinders were used to calibrate the oxygen electrode. The gas bubbling rate was controlled at (3–6 bubbles/second) by a needle valve at the flow meter.
2. Calibration of Oxygen Electrode
   a) Two separate calibration chambers were used. One for pure $N_2$ and another for pure $O_2$. Each calibration chamber contained about 30 mL DI $H_2O$.
   b) DI $H_2O$ present in the chamber (which had been sparged with gas) was drawn by the peristaltic pump through the flow-thru housing and back into the chamber in a continuous stream.
   c) After a stable reading was obtained with bubbling pure $N_2$ in DI $H_2O$, the oxygen meter was zeroed.
   d) Tubing set from the first calibration chamber was removed and placed onto second calibration chamber for bubbling the pure $O_2$ through the chamber (at a constant rate of about 3–6 bubbles/second).
   e) Oxygen saturated DI $H_2O$ was pumped through the flow-thru housing at the same flow rate as that used in step 2b.
   f) After a stable reading was obtained, the calibration in oxygen meter was adjusted to 100.0, signifying a 100% saturation.
   g) The above steps were repeated until readings became stable and reproducible.
3. Sample Test
   a) Tubing set was removed from the calibration chamber and placed onto a 50 mL container, similar to the calibration chamber. This container was filled with 30 mL of fresh media and sparged with pure $O_2$. Media in the container was drawn out through the flow-thru housing and pumped back to the container. A stable reading obtained from the oxygen meter indicated the effect of media composition on the dissolved oxygen relative to the 100% saturation of dissolved oxygen in DI $H_2O$.
   b) After disconnecting the liquid flowpath at A (male and female connectors), a test tube containing 3 mL of ECS harvest was connected (at B) into the flowpath.
   c) The tubing downstream of the flow-thru housing was placed into a sample reservoir.
   d) A sample in the test tube was delivered through the flow-thru housing and collected in the sample reservoir. The peristaltic pump controlled the media flow rate so that an equivalent electrode response time as that for standards was achieved.
   e) After a stable reading was recorded, a second sample was tested by following the procedure from step 3b to 3d.

f) DI H$_2$O was pumped through the flow-thru housing with about 10 mL to clean the oxygen electrode membrane. Finally, the pump and oxygen meter were switched off.

Figure 22:
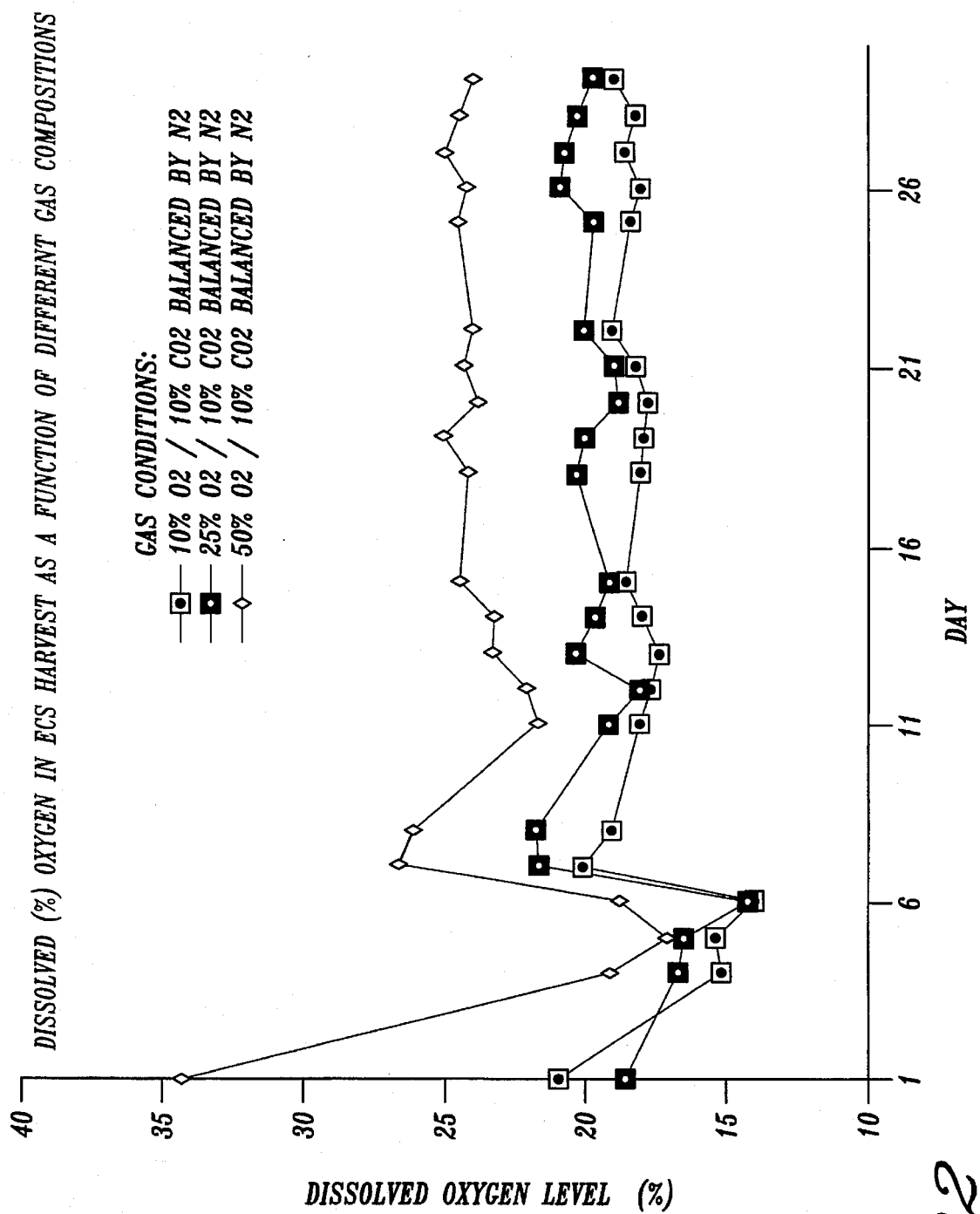
FIG. 22 illustrates the effect of oxygen composition in the gas supplied to oxygenator fibers of the HPBr.

FIG. 22 illustrates the effect of oxygen composition in the gas supplied to oxygenator fibers of HPBr. It also shows the impact of days in culture (i.e., cell mass, product accumulation in the ECS, and the like), on dissolved oxygen profile.

Generally, as oxygen content in the gas increased, so too did the dissolved oxygen. However, there was typically a decline in dissolved oxygen to reach a minimum within the first 5–6 days in culture (the time required to achieve steady state).

The final, or average DO value after day 5 increased as oxygen composition in the gas increased. Therefore, cells were cultured in an oxygen rich (i.e., highly aerobic environment).

longitudinal axis of the device was done continuously at 30 cpm (i.e., to-and-fro at 120°); 2) several hours after inoculation the gas pressure was increased from 1.5 to 5 psi (to simulate failure mode) then returned to 1.5 psi after about 6 hours. The experiment was run for 7 days.

Materials

Culture media: AIM-V (Life Technologies, Grand Island, N.Y.)

Growth factor: Recombinant IL-2 (Cetus Corp., Emeryville, Calif.)

Antibody: Anti-CD3

Media supplement: L-glutamine (Life Technologies, grand Island, N.Y.)

Benzoate buffer: Sodium benzoate/benzoic acid (2.5 mM), Sigma Chemical Co.

TABLE 8

Effect of Oxygen Content on IgG1 Concentration in HPBr*

| Five Day Period | Data From Example III | | Run 2 | Run 3 | Run 4 | Run 5 | Run 6 |
| | Run 1 | Run 3 | | | | | |
| | | | Oxygen Content in Gas | | | | |
| | 10% | 19% | 25% | 50% | 75% | 90% | 90% |
| | | (Average IgG1 Concentration, mg/mL) | | | | | (0.001 M.S.B.) |
| 0 | 0 | 0/0 | 0 | 0 | 0 | 0 | 0 |
| 1–5 | 0.61 | 0.43/0.63 | 0.62 | 0.70 | 0.70 | 0.63 | 0.47 |
| 6–10 | 0.81 | 0.94/0.77 | 0.84 | 0.92 | 1.0 | 0.86 | 0.69 |
| 11–15 | 0.64 | 0.92/0.66 | 0.69 | 0.69 | 0.60 | 0.34 | 0.70 |
| 16–20 | 0.56 | 0.85/0.44 | 0.60 | 0.52 | 0.38 | 0.23 | 0.73 |
| 21–25 | 0.41 | 0.87/0.44 | 0.33 | 0.20 | 0.38 | 0.34 | 0.56 |
| 26–30 | 0.45 | 0.56/0.45 | 0.31 | 0.19 | 0.19 | 0.16 | 0.74 |
| Cumulative IgG1 (mg) | 168.8 | 228.4/169.1 | 164.2 | 155.5 | 164.6 | 131.1 | 194.6 |

*A premixed gas cylinder with 10% CO$_2$ and different percentage of O$_2$ balanced by N$_2$ (as required) was used and each HPBr had 450 cellulose media fibers and 540 polypropylene oxygenating fibers.

Table 8 shows the effect of oxygen content of the gas supplied to oxygenating fibers of HPBr on cumulative IgG1 production and IgG1 concentration, with and without 0.001 M sodium benzoate in the ICS media, respectively.

At high oxygen content there was higher initial IgG1 concentration and hence cumulative production for the first 10 days. Subsequently, decline in IgG1 concentration (for all gas compositions tested), was more dramatic at higher oxygen composition.

This is interpreted as resulting from the long-term effect of increased concentrations of free radicals (O$_2$) on cell viability. Hence, sodium benzoate (free radical scavenger) dramatically reduced the extent to which IgG1 concentration declined after day 10. This is supported by the larger fold increase after 30 days in culture for run 6 (with 0.001 M sodium benzoate), compared with run 5 (without sodium benzoate).

EXAMPLE VII

One high performance bioreactor containing 450 10 kD cellulosic fibers and 540 polypropylene oxygenator fibers was compared with two 250 mL gas permeable bags, Cryocyte (code 4R5461 from Baxter). Human T-lymphocytes were prepared for inoculation by standard centrifugation and density gradient (ficol) separation methods.

Gas permeable bags were maintained at 37° C. in a 5% CO$_2$ incubator for 7 days. The bioreactor was operated as described previously, except that: 1) rotation around the Antibiotic: Penicillin/streptomycin (Life Technologies, Grand Island, N.Y.)

Stain for counting fixed T-cells: DIF-QUIK (Sigma Chemical Co., St. Louis, Mo.)

| Culture Conditions | Bag #1 | Bag #2 | HPBr |
| --- | --- | --- | --- |
| 1. Media volume | 50 mL | 20 mL | 17 mL (ECS) |
| 2. L-Glutamine | 2.2 mM | 4 mM | 4 mM |
| 3. Benzoate buffer | None | 2.5 mM | 2.5 mM |
| 4. Antibody (anti-CD3) | 10 µg/mL | 10 µg/mL | 6.3 µg/mL |
| 5. Cells devoid of media | N/A | N/A | 6 hr |
| 6. Inoculum (viable) | $2.5 \times 10^6$ | $3.3 \times 10^7$ | $5.0 \times 10^7$ |
| Results | | | |
| 7. Harvest (viable) | $8.9 \times 10^5$ | $8.1 \times 10^5$ | $1.9 \times 10^7$ |

Bag #1 represents the current state of the art for lymphocyte cultivation in a scaleable device and method. Bag #2 serves as a control that illustrates the negative effect of relatively high density cell culture in gas permeable bags. It also distinguishes between the effect of the benzoate buffer and the relative performance of the HPBr compared with the gas permeable bag device at high cell densities.

Cells were harvested from the HPBr ECS) by expelling the contents with sterile air from a syringe barrel, and likewise flushing the ECS with fresh media. The two fractions were pooled, washed, and analyzed.

The HPBr performed equivalently at higher cell densities, compared with the gas permeable bag (#1). This was in spite of a 6 hr period (only hours after inoculation), during which media was forced out of the ECS when gas pressure was increased to 5 psi. On returning the gas pressure to about 1.5 psi, media returned to the ICS. The condition simulated in this experiment is one of the most serious failure modes suggested by clinicians for the HPBr. Loss of a patent's T-lymphocytes is a life and death issue. Performance of the HPBr for T-lymphocyte expansion can be significantly improved by those skilled in the art. Furthermore, cost reductions can be achieved as lower quantities of expensive reagents (e.g., anti-CD3) are required.

EXAMPLE VIII

A high performance bioreactor that was fabricated with a port in the flow distributor plate (for inoculating into the inner annular space of the ECS), was employed to cultivate freshly isolated porcine hepatocytes for 5 weeks. The device contained 450 10 kD cellulose fibers 540 polypropylene fibers. Cells were isolated by a method based on procedures for rat liver reported in "Methods in Cell Biology, volume XIII", edited by D. M. Prescott, Academic Press, 1976.

Materials

All materials were obtained from either Sima Chemical Co. or Life Technologies.

| Attachment Media | Long-term Culture Media |
| --- | --- |
| CPMI 1640 (500 mL) | CPMI 1640 (500 mL) |
| 50 mL (10%) FBS | No serum |
| 4 mM L-glutamine | 4 mM L-glutamine |
| 1x Penicillin/streptomycin | 1x Penicillin/streptomycin |
| 50 µg/mL Gentamicin | 50 µg/mL Gentamicin |
| 15 mM HEPES | 15 mM HEPES |
| 10 mU/mL Insulin | 10 mU/mL Transferrin |
| 6 µg/mL Transferrin | 6 µg/mL Transferrin |
| 6 µg/mL Selenium | 6 µg/mL Selenium |

The HPBr system was flushed with media for one day before attachment media was applied. 500 mg of preswollen Cytodex 3 microcarriers was inoculated in the inner annular space of the HPBr. The oxygenator fibers cradled the microcarriers and prevented them from distributing throughout the ECS. $1 \times 10^9$ viable porcine hepatocytes were also inoculated into the inner annular space, and the device rocked and rotated by hand to achieve uniform mixing of cells and microcarriers. Assuming that the hepatocytes are between 15–20 µm diameter, the cell-to-microcarrier inoculum ratio was about 500. The apparent viscosity of cells and microcarriers was observed to increase rapidly, suggesting that cell-to-microcarrier and possibly cell-to-cell attachments were proceeding rapidly. Within a 2–3 minutes of this mixing a discrete gel of cells and microcarriers was formed in the inner annular space only.

Following an overnight incubation at 37° C. in attachment media (in a stationary position), the media was changed to long-term culture media (2 L). The hepatocytes were cultured for 5 weeks, with fresh media applied to the system weekly. The metabolic function of the cells was monitored by testing daily samples.

After 5 weeks, >90% recovery of viable cells and microcarriers was achieved by the following procedure:

1. 0.1% collagenase in PBS mixed with 0.44 mL (0.23 M) EDTA was used to flush the ECS and the HPBr incubated at 37° C. to 10 minutes.
2. The content of the ECS was expelled with sterile air from a syringe barrel.
3. This process was repeated with long-term culture media and the materials collected washed and separated.

EXAMPLE IX

The HPBr can be employed in the cultivation and genetic transformation of cells (e.g., beta-galactosidase gene expression). The following is a genetic non-viral protocol for anchorage dependent cells (e.g., SW 480 P3; ATCC #CCL228), that can be appropriately modified and optimized from published procedures using culture wells and dishes, by those skilled in the art. Media fiber with 10 kD properties are preferred in the HPBr. Operate the bioreactor in much the same manner as previously described. Cytodex 1 microcarrier (Pharmacia, sold by Sigma Chemical Co.) is widely use for culturing anchorage dependent cells.

1. A broad range of cell densities can be inoculated into the ECS of the HPBr, ranging from:$<1 \times 10^4$ to$>1 \times 10^{10}$. The recommended cell-to-microcarrier inoculum ratio is in the range of about 10. After mixing cells and microcarriers thoroughly, about a few hours of incubation in a static position may improve cell attachment efficiency.
2. The device is gently rotated throughout the experiment at about 10 cpm (or greater).
3. After culturing the cells for about one day (or more, depending on the specific cell), optimal confluence should be attained to obtain efficient transfection. The cell-to-microcarrier inoculation ratio can be adjusted to positively impact this time frame for therapeutic and economic efficiency.
4. On the day of the transfection, prepare the DNA plasmid solution (e.g., pCMV beta-gal), and cationic lipid solution (e.g., LIPOFECTIN Reagent, Life Technologies). These reagents most be serum free, even if the overall process requires the presence of serum.
5. Mix appropriate quantities of DNA and lipid solutions, then inject the mixture into the ECS of the device.
6. After about a few (or even several) hours of transfection, resume use of serum, if appropriate, and continue to culture cells as before for about a few days. [Longer periods may be used when expanding permanently transformed cells].
7. Harvest cells in a manner similar to that described previously.

While preferred embodiments of the invention have been illustrated and described, it will be appreciated that various changes can be made therein without departing from the spirit and scope of the invention.

The embodiments of the invention in which an exclusive property or privilege is claimed are defined as follows:

1. A bioreactor comprising:

a housing comprising an inner wall defining a substantially tubular cell culture chamber, first and second ends defining a longitudinal axis through said chamber, and a port providing access to said chamber, a central bundle of porous hollow fibers disposed around the longitudinal axis within said chamber, an annular bundle of gas permeable hollow fibers disposed concentric to and surrounding said central bundle, means disposed at said first and second ends for passing nutrient media through said porous hollow fibers, and means disposed at said first and second ends for passing an oxygen containing gas through said gas permeable hollow fibers.

2. The bioreactor of claim 1, wherein an annular space is provided between said inner wall and said annular bundle.

3. The bioreactor of claim 2, further comprising a plurality of microcarriers within said annular space.

4. The bioreactor of claim 1, wherein an annular space is provided between said annular bundle and said central bundle.

5. The bioreactor of claim 4, further comprising a plurality of microcarriers within said annular space.

6. The bioreactor of claim 1, wherein the ratio of the surface area of said gas permeable hollow fibers to the surface area of said porous hollow fibers is from about 0.5 to about 3.1, and wherein said gas permeable hollow fibers and said porous hollow fibers collectively occupy from about 10 to about 40 percent by volume of the cell culture chamber.

7. The bioreactor of claim 6, wherein the ratio of the surface area of said gas permeable hollow fibers to the surface area of said porous hollow fibers is from about 0.5 to about 1.5, and wherein said gas permeable hollow fibers and said porous hollow fibers collectively occupy from about 10 to about 25 percent by volume of the cell culture chamber.

8. The bioreactor of claim 6, wherein the ratio of the surface area of said gas permeable hollow fibers to the surface area of said porous hollow fibers is from about 1.5 to about 3.1, and wherein said gas permeable hollow fibers and said porous hollow fibers collectively occupy from about 25 to about 40 percent by volume of the cell culture chamber.

9. The bioreactor of claim 1, wherein the ratio of the surface area of said gas permeable hollow fibers to the surface area of said porous hollow fibers is from about 3.1 to about 4, and wherein said gas permeable hollow fibers and said porous hollow fibers collectively occupy from about 40 to about 50 percent by volume of the cell culture chamber.

10. The bioreactor of claim 1, wherein the ratio of the surface area of said gas permeable hollow fibers to the surface area of said porous hollow fibers is from about 4 to about 5.8, and wherein said gas permeable hollow fibers and said porous hollow fibers collectively occupy from about 50 to about 70 percent by volume of the cell culture chamber.

11. A kit comprising a bioreactor of claim 2 and a plurality of microcarriers.

12. The kit of claim 11, wherein said microcarriers are coated with an extracellular matrix.

13. A kit comprising a bioreactor of claim 6 and a plurality of microcarriers.

14. A kit comprising a bioreactor of claim 9 and a plurality of microcarriers.

15. A kit comprising a bioreactor of claim 4 and a plurality of microcarriers.

16. The kit of claim 15, wherein said microcarriers are coated with an extracellular matrix.

17. A method of cell culture comprising:
introducing cells into the cell culture chamber of a bioreactor of claim 1, and
incubating said cells within said chamber while passing an oxygen containing gas through said gas permeable hollow fibers and while passing nutrient media through said porous hollow fibers.

18. The method of claim 17, wherein the passage of oxygen containing gas through said gas permeable hollow fibers is counter current to the passage of nutrient media through said porous hollow fibers.

19. The method of claim 17 wherein during said incubation step the bioreactor is periodically rotated to-and-fro around its longitudinal axis.

20. The method of claim 17, wherein said nutrient media contains a free radical scavenger.

21. The method of claim 20, wherein said free radical scavenger is selected from among the group consisting of sodium benzoate and benzoic acid.

22. The method of claim 20, wherein said free radical scavenger is present in said nutrient media at a concentration of from about 0.001 to about 0.1 M.

23. The method of claim 22, wherein said nutrient media containing said free radical scavenger is buffered to maintain pH at about 7.1.

24. The method of claim 17, wherein said oxygen containing gas is passed through said gas permeable hollow fibers at a pressure low enough to avoid formation of gas bubbles within the cell culture chamber.

25. The method of claim 24, wherein said pressure is from about 0.5 to about 1.5 psi.

26. The method of claim 17, wherein said bioreactor comprises an annular space between said inner wall and said annular bundle, and wherein said cells are introduced through said port into said annular space.

27. The method of claim 26, wherein a plurality of microcarriers are provided in said annular space.

28. The method of claim 17, wherein said bioreactor comprises an annular space between said annular bundle and said central bundle, and wherein said cells are introduced through said port into said annular space.

29. The method of claim 28, wherein a plurality of microcarriers are provided in said annular space.

30. The method of claim 17, further comprising:
harvesting said cells from said chamber.

31. The method of claim 30, wherein said bioreactor comprises a first port adjacent said first end and a second port adjacent said second end, and wherein said harvesting step comprises introducing a gas through the first port into the chamber and thereby displacing medium containing cells from the chamber through the second port.

32. The method of claim 30, wherein said harvesting step comprises introducing a proteolytic enzyme into the chamber.

33. The method of claim 32, wherein the proteolytic enzyme is selected from among the group consisting of trypsin and collagenase.

34. A bioreactor comprising:
a housing comprising an inner wall defining a substantially tubular cell culture chamber, the chamber having first and second ends, a longitudinal axis, and a port providing access to said chamber;
a central bundle of porous hollow fibers surrounding the longitudinal axis of said chamber, each of the fibers in fluid communication with a common axially-extending liquid inlet port; and
an annular bundle of gas permeable hollow fibers disposed concentric with, and surrounding, said central bundle, each of the gas permeable fibers of the annular bundle having an outlet end and an inlet end, the outlet ends of the gas permeable fibers in fluid communication with a common annular space surrounding the axially-extending liquid inlet port, a gas outlet port in fluid communication with the common annular space.

35. The bioreactor of claim 34, wherein the annular bundle is spaced from the inner wall of the cell culture chamber to provide a cell culture annular space.

36. The bioreactor of claim 35, further comprising a plurality of microcarriers within said cell culture annular space.

37. The bioreactor of claim 34, wherein the ratio of the surface area of said gas permeable hollow fibers to the surface area of said porous hollow fibers is from about 0.05 to about 3.1.

38. The bioreactor of claim 37, wherein the central bundle of porous hollow fibers and the annular bundle of gas permeable fibers collectively occupy about 10 to about 40% by volume of the chamber.

39. The bioreactor of claim 34, wherein the ratio of the surface area of the gas permeable fibers to the hollow fibers is from about 0.5 to about 1.5

40. The bioreactor of claim 39, wherein the annular bundles of gas permeable hollow fibers and the central bundle of porous hollow fibers occupy collectively from about 10 to about 25% by volume of the cell culture chamber.

41. The bioreactor of claim 34, wherein the ratio of the surface area of said gas permeable hollow fibers to the surface area of said porous hollow fibers is from about 1.5 to about 3.1.

42. The bioreactor of claim 41, wherein the central bundle and the annular bundle collectively occupy from about 25 to about 40% of the volume of the cell culture chamber.

43. The bioreactor of claim 34, wherein the ratio of the surface area of the gas permeable hollow fibers to the porous hollow fibers is from about 4 to about 5.8.

44. The bioreactor of claim 43, wherein the gas permeable fibers and the porous fibers collectively occupy from about 50 to about 70% by volume of the cell culture chamber.

45. The bioreactor of claim 34, wherein the central bundle is spaced from the annular bundle.

46. The bioreactor of claim 35, wherein the central bundle is spaced from the annular bundle.

* * * * *

UNITED STATES PATENT AND TRADEMARK OFFICE
CERTIFICATE OF CORRECTION

| | | |
|---|---|---|
| PATENT NO. : | 5,622,857 | Page 1 of 5 |
| DATED : | April 22, 1997 | |
| INVENTOR(S) : | R.A. Goffe | |

It is certified that error appears in the above-identified patent and that said Letters Patent is hereby corrected as shown below:

| COLUMN | LINE | |
|---|---|---|
| 1 | 4 | "APLICATIONS" should read --APPLICATIONS-- |
| 1 | 6 | "applicstion" should read --application-- |
| 1 | 6 | after "continuation-in-part" insert --under 35 U.S.C. § 120-- |
| 1 | 6 | "appliation" should read --application-- |
| 2 | 4 | "(CUR)" should read --(GUR)-- |
| 2 | 15 | "ofICS" should read --of ICS-- |
| 3 | 23 | "II provide" should read --II provide-- |
| 3 | 50 | "comains" should read --contains-- |
| 4 | 26 | "of high" should read --of a high-- |

UNITED STATES PATENT AND TRADEMARK OFFICE
CERTIFICATE OF CORRECTION

PATENT NO. : 5,622,857
DATED : April 22, 1997
INVENTOR(S) : R.A. Goffe

It is certified that error appears in the above-identified patent and that said Letters Patent is hereby corrected as shown below:

| COLUMN | LINE | |
|---|---|---|
| 5 | 4 | "illustrate the" should read --illustrates the-- |
| 5 | 31 | "BOREACTOR" should read --BIOREACTOR-- |
| 5 | 43 | "FIGS. 2 and 2A illustrates" should read --FIGS. 2 and 2A illustrate-- |
| 5 | 47 | "tteader" should read --Header-- |
| 6 | 6 | "4¾" should read --4 ¾-- |
| 6 | 28 | "FIGtIRE 4" should read --FIG. 4-- |
| 7 | 49 | "a HPBr" should read --an HPBr-- |
| 7 | 57 | "ceils" should read --cells-- |
| 7 | 62 | "Type III" should read --Type III-- |
| 8 | 44 | "dependent of" should read --dependent on-- |

UNITED STATES PATENT AND TRADEMARK OFFICE
CERTIFICATE OF CORRECTION

PATENT NO. : 5,622,857
DATED : April 22, 1997
INVENTOR(S) : R.A. Goffe

It is certified that error appears in the above-identified patent and that said Letters Patent is hereby corrected as shown below:

| COLUMN | LINE | |
|---|---|---|
| 9 | 42 | "fibers facilitates" should read --fibers facilitate-- |
| 10 | 58 | "(n)at" should read --(n) at-- |
| 11 | 65 | "week and" should read --week at-- |
| 13 | 57 | "20 raM" should read --20 mM-- |
| 14 | 7 | "CUR" should read --GUR-- |
| 14 | 57 | "carded" should read --carried-- |
| 15 | 41 | "YECS" should read --ECS-- |
| 16 | 39 | "was replace" should read --was replaced-- |
| 17 | 2 | after "For Example" insert --,-- |
| 17 | 14 | "LPK" should read --LPR-- |

UNITED STATES PATENT AND TRADEMARK OFFICE
CERTIFICATE OF CORRECTION

PATENT NO. : 5,622,857             Page 4 of 5
DATED : April 22, 1997
INVENTOR(S) : R.A. Goffe It is certified that error appears in the above-identified patent and that said Letters Patent is hereby corrected as shown below:

| COLUMN | LINE | |
|---|---|---|
| 17 | 45 | "Eaglep's" should read --Eagle's-- |
| 18 | 35 | "benzoate was" should read --benzoate were-- |
| 18 | 59 | "hybfidoma" should read --hybridoma-- |
| 22 | 14 | "grand Island" should read --Grand Island-- |
| 22 | 62 | "HPBr ECS)" should read --HPBr (ECS)-- |
| 23 | 6 | "of a patent's" should read --of a patient's-- |
| 23 | 34 | "50 µg/mL" (second occurrence) should read --10 µg/mL-- |
| 23 | 52 | "a 2-3 minutes" should read --2-3 minutes-- |
| 24 | 14 | "widely use" should read --widely used-- |
| 24 | 34 | "most be" should read --must be-- |

UNITED STATES PATENT AND TRADEMARK OFFICE
CERTIFICATE OF CORRECTION

PATENT NO. : 5,622,857
DATED : April 22, 1997
INVENTOR(S) : R.A. Goffe

It is certified that error appears in the above-identified patent and that said Letters Patent is hereby corrected as shown below:

| COLUMN | LINE | |
|---|---|---|
| 26 (Claim 32, | 36 line 1) | "claim30," should read --claim 30-- |
| 27 (Claim 39, | 9 line 3) | "1.5" should read --1.5.-- |

Signed and Sealed this

Twenty-first Day of April, 1998

Attest:

BRUCE LEHMAN

Attesting Officer        Commissioner of Patents and Trademarks